United States Patent [19]

Wettlaufer et al.

[11] Patent Number: 5,114,936
[45] Date of Patent: May 19, 1992

[54] 6,7-DIHYDRO-3-PHENYL-1,2-BENZISOX-AZOL-4(5H)-ONES AND -OLS, COMPOSITIONS AND PHARMACEUTICAL USE

[75] Inventors: David G. Wettlaufer, Phillipsburg; Gregory M. Shutske, Flemington; Peter A. Nemoto, Piscataway, all of N.J.

[73] Assignee: Hoechst-Roussel Pharmaceuticals Incorporated, Somerville, N.J.

[21] Appl. No.: 692,341

[22] Filed: Apr. 26, 1991

Related U.S. Application Data

[63] Continuation-in-part of Ser. No. 571,482, Jun. 20, 1990, abandoned.

[51] Int. Cl.$^5$ .................. A61K 31/42; A61K 31/535; C07D 261/20; C07D 413/06
[52] U.S. Cl. .................. 514/233.8; 514/253; 514/254; 514/318; 514/321; 514/374; 544/137; 544/295; 544/364; 544/368; 546/194; 546/198; 548/241
[58] Field of Search .............. 544/137, 295, 364, 368; 546/194, 198; 548/241; 514/233.8, 253, 254, 318, 321, 379

[56] References Cited

U.S. PATENT DOCUMENTS 4,010,176  3/1977  Kulsa et al. .................. 548/247

FOREIGN PATENT DOCUMENTS 2024008  1/1980  United Kingdom .

Primary Examiner—Robert W. Ramsuer
Attorney, Agent, or Firm—Elliott Korsen

[57] ABSTRACT

This invention relates to 6,7-dihydro-3-phenyl-1,2-benzisoxazol-4(5H)-ones and -ols of the formula

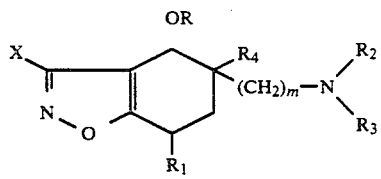

wherein X is (Y)

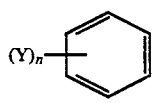

or loweralkyl; Y is hydrogen, halogen, loweralkyl, loweralkoxy, trifluoromethyl, nitro or amino; R is H when the bond between the oxygen atom and the carbon atom in question is a single bond; otherwise the dotted line signifies part of a double bond to the oxygen atom; $R_1$ is hydrogen, loweralkyl or arylloweralkyl; $R_2$ and $R_3$ are independently hydrogen, lower alkyl or arylloweralkyl, or $R_2$ and $R_3$ taken together with the nitogen atom form an optionally substituted heterocycle selected from the group consisting of piperidinyl, pyrrolidinyl, morpholinyl, imidazol-1-yl, 1-piperazinyl, said substituents being hydrogen or loweralkyl; 4-substituted-1-piperazinyl of the formula

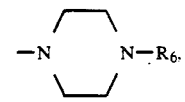

where $R_6$ is loweralkyl, aryl, arylloweralkyl,

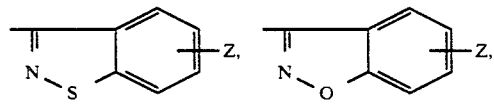

2-pyrimidyl,

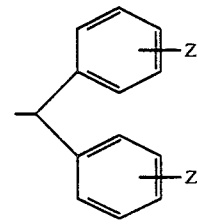

2-pyridinyl of the formula

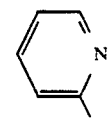

or 4-pyridinyl of the formula

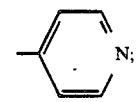

4-substituted-1-piperidinyl of the formula

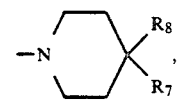

wherein $R_7$ is hydrogen, loweralkyl, aryl, arylloweralkyl, 2-pyridinyl of the formula 4-pyridinyl of the formula

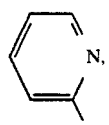

2-pyrimidinyl of the formula

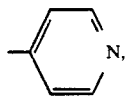

arylcarbonyl,

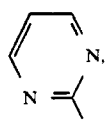

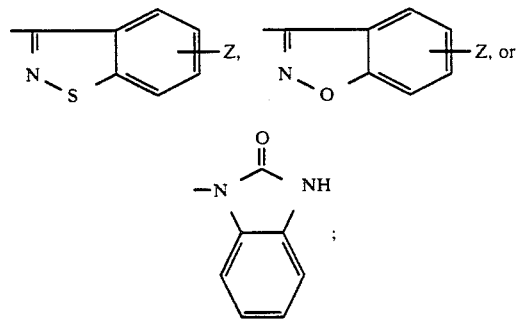

$R_8$ is hydrogen or —OH; $R_4$ is hydrogen, loweralkoxycarbonyl or aryloxycarbonyl; Z is chlorine, bromine or fluorine; m is an integer of 1 to 4; n is an integer of 1 to 4 or a pharmaceutically acceptable acid addition salt thereof and where applicable the geometric and optical isomers and racemic mixtures thereof. The compounds of this invention display utility as antipsychotic agents and analgesic agents.

47 Claims, No Drawings

6,7-DIHYDRO-3-PHENYL-1,2-BENZISOXAZOL-4(5H)-ONES AND -OLS, COMPOSITIONS AND PHARMACEUTICAL USE

This is a continuation-in-part application of pending application U.S. Ser. No. 571,482, filed Jun. 20, 1990, now abandoned.

This invention relates to 6,7-dihydro-3-phenyl-1,2-benziosxazol-4(5H)-ones and -ols of the formula

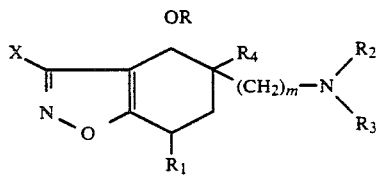

wherein X is

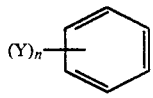

or loweralkyl; Y is hydrogen, halogen, loweralkyl, loweralkoxy, trifluoromethyl, nitro or amino; R is H when the bond between the oxygen atom and the carbon atom in question is a single bond; otherwise the dotted line signifies part of a double bond to the oxygen atom; $R_1$ is hydrogen, loweralkyl or aryloweralkyl; $R_2$ and $R_3$ are independently hydrogen, loweralkyl or aryloweralkyl, or $R_2$ and $R_3$ taken together with the nitrogen atom form an optionally substituted heterocycle selected from the group consisting of piperidinyl, pyrrolidinyl, morpholinyl, imidazol-1-yl, 1-piperazinyl, said substituents being hydrogen or loweralkyl; 4-substituted-1-piperazinyl of the formula

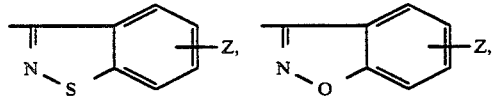

where $R_6$ is loweralkyl, aryl, aryloweralkyl,

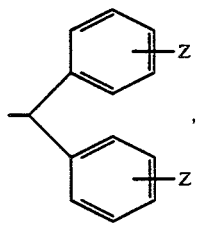

2-pyridinyl of the formula

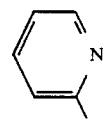

or 4-pyridinyl of the formula

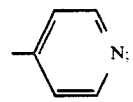

4-substituted-1-piperidinyl of the formula

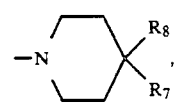

wherein $R_7$ is hydrogen, loweralkyl, aryl, aryloweralkyl, 2-pyridinyl of the formula

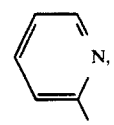

4-pyridinyl of the formula

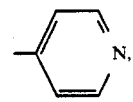

2-pyrimidinyl of the formula

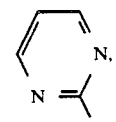

arylcarbonyl,

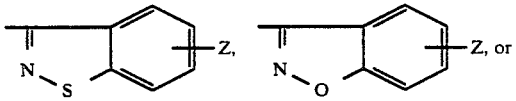

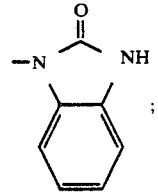

$R_8$ is hydrogen or —OH; $R_4$ is hydrogen, loweralkoxycarbonyl or aryloxycarbonyl; Z is chlorine, bromine or fluorine; m is an integer of 1 to 4; n is an integer of 1 to 4 or a pharmaceutically acceptable acid addition salt thereof and where applicable the geometric and optical isomers and racemic mixtures thereof. The compounds of this invention display utility as antipsychotic agents and analgesic agents.

Throughout the specification and appended claims, a given chemical formula or name shall encompass all geometric and stereoisomers and racemic mixtures where such isomers and mixtures exist.

The term loweralkyl shall mean a straight or branched alkyl group having from 1 to 6 carbon atoms. Examples include methyl, ethyl, n-propyl, isopropyl, n-butyl, t-butyl and straight and branched chain pentyl and hexyl.

The term aryl shall means a phenyl group optionally substituted with one or more halogen, loweralkyl, loweralkoxy or trifluoromethyl groups, including m-methoxyphenyl.

The term halogen shall mean fluorine, chlorine, bromine or iodine.

The compounds of the present invention, wherein X is phenyl, are prepared in the following manner. The substituents R, $R_1$, $R_2$, $R_3$, $R_4$, X, Y and Z and the integers m and n are as defined above unless indicated otherwise.

A substituted benzaldehyde is selected having the formula

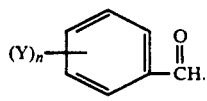

(II)

Such benzaldehydes are well known or can be synthesized by conventional techniques well known by one of ordinary skill in the art. Compound II is reacted with hydroxylamine hydrochloride, under conventional oxime formation conditions, to form the oxime, Compound III, having the formula

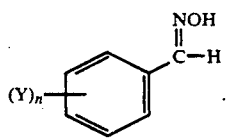

(III)

Typically, this reaction is conducted in a basic aromatic solvent, such as pyridine, picoline or collidine, at about room temperature to 100° C. for 0.5 to 2 hours.

Oxime III is reacted with a halogen such as $Cl_2$ or $Br_2$ to form a halo-oxime of the formula

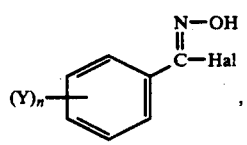

(IV)

where Hal is a halogen selected from Cl and Br. Typically, this reaction is conducted in an inert solvent such as dichloromethane, chloroform or 8N HCl at a temperature of from 0° to 15° C. Gaseous halogen, e.g. $Cl_2$, is bubbled into the reaction at such a rate as to maintain the reaction temperature below 15° C. The halogen is bubbled in for a time period of from about 2 to 10 minutes whereafter; when the solvent is not 8N HCl, a triethylamine/solvent solution is added dropwise during further bubbling of the gaseous halogen until no further color changes are observed.

Compound IV is reacted with Compound V of the formula

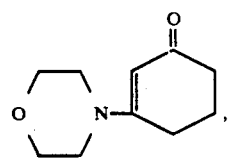

(V)

to form Compound (VI) of the formula

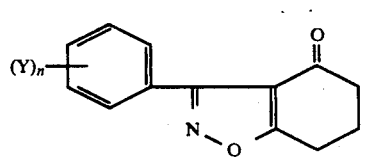

(VI)

Compound V is well known or can be synthesized by conventional techniques well known by one of ordinary skill in the art. For example, Compound V can be prepared following the techniques of Edward J. Cone et al., *J. Organic Chemistry* 37, No. 26, 4436 (1972). Typically, a 1,3-cyclohexanedione of the formula

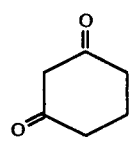

(VII)

is reacted with morpholine,

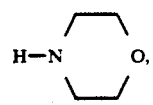

(VIII)

in an inert solvent, such as benzene or toluene, under a nitrogen atmosphere at reflux for 1 to 2 hours to obtain Compound V.

Compound IV is combined with Compound V, contained in an inert solvent such as dichloromethane or chloroform in the presence of triethylamine, present in an amount of 2 to 3 equivalents, at ambient temperature for 18 to 24 hours to obtain Compound VI.

Compound VI is reacted with an amine of the formula

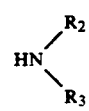

(VII)

in the presence of paraformaldehyde to form Compound VIII of the invention having the formula

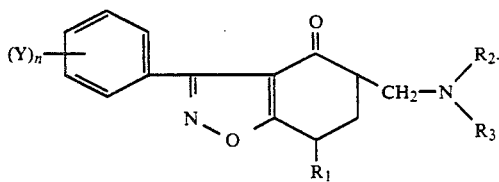
(VIII)

Typically, this reaction is conducted in an alkanolic solvent such as methanol, ethanol or isobutanol at a temperature of 25° to 100° C. for 1 to 24 hours. Alternatively Compound VIII is formed by reacting Compound VI with an amine IX of the formula

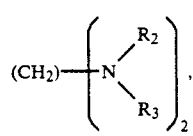
(IX)

in the presence of a strong organic acid such as trifluoroacetic or methanesulfonic acid. Typically, the reaction is conducted with the organic acid as solvent, at a temperature of 0° to 100° C. for 1 to 12 hours.

Compound VIII, where $R_2$ and $R_3$ are alkyl, may undergo a displacement reaction with a higher boiling amine, such as a base containing a heterocyclic group, e.g. a piperidinyl, pyrrolidinyl, morpholinyl, 1H-imidazol-1-yl, 1-piperazinyl, 4-substituted-1-piperazinyl or 4-substituted-1-piperidinyl group to form Compound X of the invention of the formula

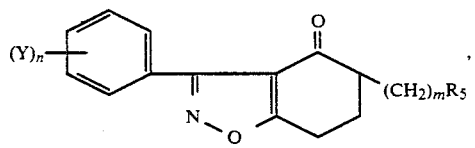
(X)

where $R_5$ is the heterocyclic group.

An intermediate in this reaction is the 5-methylene derivative (Xa) of the formula

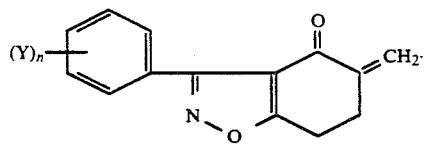
(Xa)

Compound Xa can be prepared independently by treating Compound VIII first with excess methyl iodide and then with a base such as aqueous sodium bicarbonate. In an alternative preparation of Compound X, Compound Xa is subjected to an addition reaction with the higher boiling amine, such as the base containing a heterocycle, as described above.

An alternative preparation is as follows.

Compound VI is lithiated, under conventional lithiation techniques and conditions, i.e., by reaction with an organic lithiation agent, such as lithium diisopropylamide, lithium bis(trimethylsilyl)amide or lithium dicyclohexylamide in an etheral solvent, such as diethyl ether, tetrahydrofuran or dimethoxyethane, at a temperature of −78° to 25° C. for 0.15 to 3 hours, in an inert atmosphere, e.g. nitrogen atmosphere, to form Compound XI of the formula

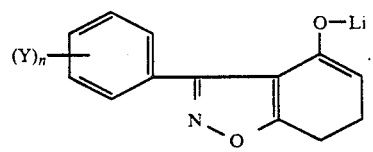
(XI)

Compound XI in turn is reacted with a dihaloalkane of the formula Hal-$(CH_2)_m$-Hal (XII), where each Hal is independently Cl, F, Br or I, e.g., 1-chloro-3-iodopropane, to form compound XIII of the formula (XIII)

Alternatively, compound XI may be reacted with a halo alkyl or halo aryl formate of the formula Hal-COO-$R_{10}$, where Hal is Cl or Br and $R_{10}$ is loweralkyl or aryl, to form compound XIIIa of the formula (XIIIa)

Typically, these reactions are carried out in an ethereal solvent such as diethylether, tetrahydrofuran or dimethoxyethane at a temperature of −78° to 25° C. for 0.5 to 24 hours.

Compound XIIIa may be further reacted with a dihaloalkane of the formula XII described above to form compound XIIIb having the formula

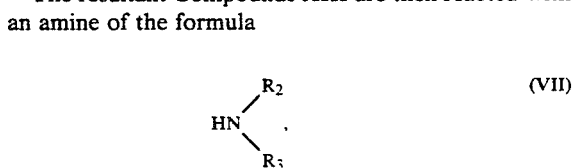
(XIIIb)

Typically, this reaction is carried out in a polar solvent such as acetone, methanol or acetonitrile in the presence of a base such as potassium carbonate, sodium carbonate, or sodium methoxide at a temperature of 0° to 100° C. for 1 to 24 hours.

The resultant Compounds XIII are then reacted with an amine of the formula

(VII)

to form a compound of the invention XIV having the formula

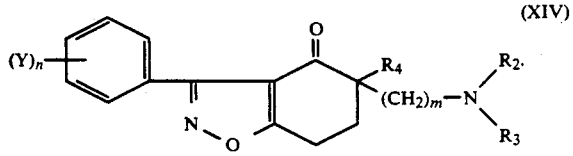

Compounds VIII, X and XIV (where $R_4$=H) may be reduced in a conventional manner, such as with a metal hydride, e.g. $NaBH_4$ or $LiBH_4$ under conventional reducing conditions to form Compounds VIII(a), X(a) and XIV(a), respectively, having the formula,

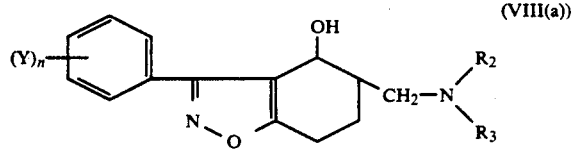

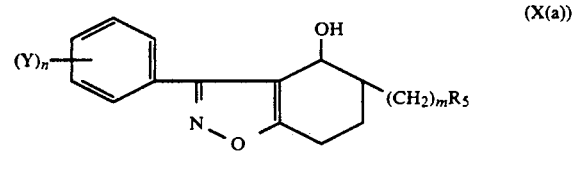

and

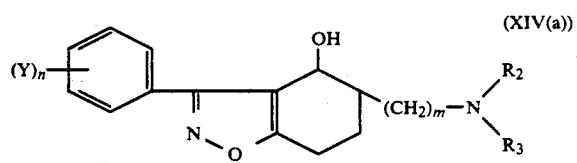

Compound XIII can be lithiated, in the manner described above, whereafter a haloalkane of the formula $R_9$ Hal where $R_9$ is loweralkyl and Hal is a halogen selected from Cl, Br and I, is reacted with the lithiated compound, in a conventional manner, to obtain Compound XV where $R_1$ is lower alkyl. Typically, the reaction is carried out in an ethereal solvent such as diethyl ether, tetrahydrofuran or 1,2-dimethoxyethane at a temperature of $-78°$ to $25°$ C. for 0.5 to 24 hours.

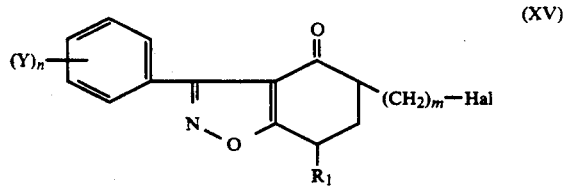

The compounds of the present invention are useful for treating psychoses by virtue of their ability to elicit an antipsychotic response in mammals.

Antipsychotic activity is determined in the Climbing Mice Assay by a method similar to that described by P. Protais, et al., *Psychopharmacol.*, 50, 1 (1976) and B. Costall, *Eur. J. Pharmacol.*, 50, 39 (1978).

The subject CK-1 male mice (23-27 grams) are group-housed under standard laboratory conditions. The mice are individually placed in wire mesh stick cages (4"×4"×10") and are allowed one hour for adaptation and exploration of the new environment. Then apomorphine is injected subcutaneously at 1.5 mg/kg, a dose causing climbing in all subjects for 30 minutes.

Compounds to be tested for antipsychotic activity are injected intraperitoneally or given orally at various time intervals, e.g. 30 minutes, 60 minutes, etc. prior to the apomorphine challenge at a screening dose of 10–60 mg/kg.

For evaluation of climbing, 3 readings are taken at 10, 20 and 30 minutes after apomorphine administration according to the following scale:

| Climbing Behavior | Score |
|---|---|
| Mice With | |
| 4 paws on bottom (no climbing) | 0 |
| 2 paws on the wall (rearing) | 1 |
| 4 paws on the wall (full climb) | 2 |

Mice consistently climbing before the injection of apomorphine will be discarded.

With full-developed apomorphine climbing, the animals are hanging on to the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneously) is set to 100%. $ED_{50}$ values with 95% confidence limits, calculated by a linear regression analysis, of some of the compounds of the instant invention as well as a standard antipsychotic agent are presented in Table I.

TABLE I

| CLIMBING MOUSE ASSAY | |
|---|---|
| COMPOUND | ($ED_{50}$ mg/kg, ip) |
| 6,7-dihydro-5-[3-(4-(2-methoxyphenyl)-1-piperazinyl)-propyl]-3-phenyl-1,2-benzisoxazol-4(5H)-one dihydrochloride | 15.0 |
| 6,7-dihydro-5-[3-(4-(4-fluorophenyl)-1-piperidinyl)-propyl]-3-phenyl-1,2-benzisoxazol-4(5H)-one hydrochloride | 6.36 |
| 6,7-dihydro-5-[3-(4-(4-fluorobenzoyl)-1-piperidinyl)-propyl]-3-(2-fluorophenyl)-1,2-benzisoxazol-4(5H)-one hydrochloride | 2.9 |
| 6,7-dihydro-5-[3-(4-(4-fluorobenzoyl)-1-piperidinyl)-propyl]-3-(4-fluorophenyl)-1,2-benzisoxazol-4(5H)-one hydrochloride | 6.2 |
| 6,7-dihydro-5-[3-(4-(4-fluorobenzoyl)-1-piperidinyl)-propyl]-3-(3-fluorophenyl)-1,2-benzisoxazol-4(5H)-one hydrochloride | 5.7 |
| clozapine (standard) | 9.0 |

Antipsychotic response is achieved when the compounds of the present invention are administered to a subject requiring such treatment of an effective oral, parenteral or intravenous dose of from 0.10 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosage range set forth herein is exemplary only and does not, to any extent, limit the scope or practice of the invention.

Compounds of the present invention are also useful as analgesics due to their ability to alleviate pain in mammals as demonstrated in the phenyl-p-quinone writhing assay in mice, a standard assay for analgesia [*Proc. Soc. Exptl. Biol. Med.* 95, 729 (1957)]

The analgesic activity of some of the compounds of the present invention expressed in terms of an $ED_{50}$ inhibition of writhing are given below in Table II.

TABLE II

| Compound | $ED_{50}$ Inhibition of Writhing mg/kg, s.c |
|---|---|
| 6,7-dihydro-5-[3-(4-(2-methoxyphenyl)-1-piperazinyl)-propyl]-3-phenyl-1,2-benzisoxazol-4(5H)-one dihydrochloride | 5.18 |
| 6,7-dihydro-5-[3-(4-(4-fluorobenzoyl)-1-piperidinyl)-propyl]-3-phenyl-1,2-benzisoxazol-4(5H)-one hydrochloride | 3.99 |
| propoxyphene (standard) | 3.90 |

The analgesic relief is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. It is to be understood, however, that for any particular subject, specific dosage regimens should be adjusted according to the individual need. It is further to be understood that the dosages set forth herein are examples only and that they do not to any extent limit the scope of the practice of the invention.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the 6,7-dihydro-3-phenyl-1,2-benzisoxazol-4(5H)-one or -ol derivative of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the 6,7-dihydro-3-phenyl-1,2-benzisoxazol-4(5H)-one or -ol derivative of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 6,7-dihydro-3-phenyl-1,2-benzisoxazol-4(5H)-one or -ol derivative of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the 6,7-dihydro-3-phenyl-1,2-benzisoxazol-4(5H)-one or -ol derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of some of the compounds of the invention include:

6,7-Dihydro-3-phenyl-5-[2-(1-piperidinyl)-ethyl]-1,2-benzisoxazol-4(5H)-one;

6,7-Dihydro-3-(4-fluorophenyl)-5-[2-(2-methyl-1H-imidazol-1-yl)-ethyl]-1,2-benzisoxazol-4(5H)-one;

3-(3-Chlorophenyl)-6,7-dihydro-5-[2-2(4-(4-fluorobenzoyl)-1-piperidinyl)-ethyl]-7-methyl-1,2-benzisoxazol-4(5H)-one;

6,7-Dihydro-3-(3-fluorophenyl)-5-[(4-methyl-1-piperazinyl)-methyl]-1,2-benzisoxazol-4(5H)-one;

3-(2-Chlorophenyl)-6,7-dihydro-5-[3-(4-(2-methoxyphenyl)-1-piperazinyl)-propyl]-1,2-benzisoxazol-4(5H)-one;

3-(3-Chlorophenyl)-6,7-dihydro-5-[2-(1-pyrrolidinyl)-ethyl]-1,2-benzisoxazol-4(5H)-one;

6,7-Dihydro-5-(4-dimethylaminobutyl)-3-phenyl-1,2-benzisoxazol-4(5H)-one;

6,7-Dihydro-5-(3-dimethylaminopropyl)-3-(3-fluorophenyl)-1,2-benzisoxazol-4(5H)-one;

3-(3-Chlorophenyl)-6,7-dihydro-5-[4-(1-piperidinyl)-butyl]-1,2-benzisoxazol-4(5H)-one;

6,7-Dihydro-3-(3-fluorophenyl)-7-methyl-5-[4-(1-pyrrolidinyl)-butyl]-1,2-benzisoxazol-4(5H)-one;

6,7-Dihydro-3-(3-fluorophenyl)-5-[2-(4-(2-methoxyphenyl)-1-piperazinyl)-ethyl]-1,2-benzisoxazol-4(5H)-one;

3-(3-Fluorophenyl)-4-hydroxy-5-[4-(4-methyl-1-piperazinyl)-butyl]-4,5,6,7-tetrahydro-1,2-benzisoxazole.

The following examples are for illustrative purposes and are not to be construed as limiting the invention disclosed herein. All temperatures are given in degrees centigrade unless indicated otherwise.

EXAMPLE 1

6,7-Dihydro-5-(4-morpholinylmethyl)-3-phenyl-1,2-benzisoxazol-4(5H)-one 6,7-Dihydro-3-phenyl-1,2-benzisoxazol-4(5H)-one, (2.0 g) was refluxed in 50 ml isobutanol containing 2.0 g morpholine.HCl, 1.0 g paraformaldehyde and 1 ml concentrated hydrochloric acid. After 7 hours at reflux, an additional 0.5 g paraformaldehyde was added and the reaction was allowed to reflux an additional 21 hours. The solvent was removed under reduced pressure and the residue distributed between ether and 5% HCl. The aqueous phase was separated, washed with additional ether and then made basic with solid $NaHCO_3$. The product was extracted into 1:1 ether/ethyl acetate and isolated by evaporation of the solvent under reduced pressure to give 1.82 g of 6,7-dihydro-5-(4-morpholinylmethyl)-3-phenyl-1,2-benzisoxazol-4(5H)-one, m.p. 140°–141° C.

Analysis: Calculated for $C_{18}H_{20}N_2O_3$: 69.21% C, 6.45% H, 8.97% N. Found: 69.18% C, 6.48% H, 8.90% N.

EXAMPLE 2

6,7-Dihydro-5-dimethylaminomethyl-3-phenyl-1,2-benzisoxazol-4(5H)-one hydrochloride Bis-dimethylaminomethane (0.51 g) was added to 2.5 ml of trifluoroacetic acid which had been previously chilled to −10° C. 6,7-Dihydro-3-phenyl-1,2-benzisoxazol-4(5H)-one (1.0 g) was then added and the reaction was warmed for 1 hour at 100° C. and then allowed to stand an additional 2 days at room temperature. The reaction mixture was poured into 5% HCl and washed with ether, after which the aqueous phase was treated with solid sodium bicarbonate until basic. Extraction with ether followed by drying and concentration gave an oil. The hydrochloride was formed in ethereal HCl and was recrystallized from dichloromethane/ether to give 0.95 g of 6,7-dihydro-5-dimethylaminomethyl-3-phenyl-1,2-benzisoxazol-4(5H)-one hydrochloride, m.p. 178°–180° C.

Analysis: Calculated for $C_{16}H_{18}N_2O_2.HCl$: 62.64% C, 6.24% H, 9.31% N. Found: 62.40% C, 6.22% H, 9.03% N.

EXAMPLE 3

6,7-Dihydro-5-(1-piperidinylmethyl)-3-phenyl-1,2-benzisoxazol-4(5H)-one hydrochloride hemihydrate 6,7-Dihydro-5-dimethylaminomethyl-3-phenyl-1,2-benzisoxazol-4(5H)-one hydrochloride (0.80 g) was warmed with 5 ml of piperidine (4.31 g) at 90° C. for 20 minutes. The excess piperidine was removed in vacuo and the hydrochloride was formed in ethereal HCl to give 0.95 g of 6,7-dihydro-5-(1-piperidinylmethyl)-3-phenyl-1,2-benzisoxazol-4(5H)-one hydrochloride hemihydrate, m.p. 182°–183° C.

Analysis: Calculated for $C_{19}H_{22}N_2O_2.HCl.0.5H_2O$: 64.12% C, 6.80% H, 7.87% N, Found: 63.81% C, 6.52% H, 7.71% N.

EXAMPLE 4 cis-5-(Dimethylaminomethyl)-4-hydroxy-3-phenyl-4,5,6,7-tetrahydro-1,2-benzisoxazole hydrochloride 6,7-Dihydro-5-dimethylaminomethyl-3-phenyl-1,2-benzisoxazol-4(5H)-one hydrochloride (7.5 g) was dissolved in 100 ml ethanol and treated with 5.0 g sodium borohydride. After stirring for 1 hour the reaction mixture was distributed between 5% HCl and ether. The aqueous phase was then made basic with solid sodium bicarbonate and extracted with ether. Concentration under reduced pressure gave the product as a mixture of trans and cis isomers which was chromatographed by preparative high pressure liquid chromatography (HPLC) (ethyl acetate/$CH_3CN$/diethylamine; 90:10:1) to give 2.20 g of the pure cis isomer. The hydrochloride was formed in HCl/ether and then recrystallized from methanol/ether to give 1.81 g of cis-5-(dimethylaminomethyl)-4-hydroxy-3-phenyl-4,5,6,7-tetrahydro-1,2-benzisoxazole hydrochloride, m.p. 235°–236° C.

Analysis: Calculated for $C_{16}H_{20}N_2O_2.HCl$: 62.23% C, 6.86% H, 9.07% N. Found: 62.14% C, 6.89% H, 8.89% N.

EXAMPLE 5 trans-5-(Dimethylaminomethyl)-4-hydroxy-3-phenyl-4,5,6,7-tetrahydro-1,2-benzisoxazole hydrochloride 6,7-Dihydro-5-dimethylaminomethyl-3-phenyl-1,2-benzisoxazol-4(5H)-one hydrochloride (7.5 g) was dissolved in 100 ml ethanol and treated with 5.0 g sodium borohydride. After stirring for 1 hour the reaction mixture was distributed between 5% HCl and ether. The aqueous phase was then made basic with solid sodium bicarbonate and extracted with ether. Concentration under reduced pressure gave the product as a mixture of trans and cis isomers which was chromatographed by preparative HPLC (ethyl acetate/$CH_3CN$/diethylamine; 90:10:1) to give 3.31 g of the pure trans isomer. The hydrochloride was formed in HCl/ether and then recrystallized from methanol/ether to give 2.90 g of trans-5-(dimethylaminomethyl)-4-hydroxy-3-phenyl-4,5,6,7-tetrahydro-1,2-benzisoxazole hydrochloride, m.p. 231°–232° C.

Analysis: Calculated for $C_{16}H_{20}N_2O_2.HCl$: 62.23% C, 6.86% H, 9.07% N. Found: 61.72% C, 6.71% H, 9.00% N.

EXAMPLE 6

6,7-Dihydro-5-methylene-3-phenyl-1,2-benzisoxazol-4(5H)-one 6,7-Dihydro-5-dimethylaminomethyl-3-phenyl-1,2-benzisoxazole-4(5H)-one free base (3.0 g) was dissolved in 3 ml of methanol and added in one portion to 5 ml (excess) of methyl iodide. As the quaternary iodide began to separate, additional methanol was added to facilitate stirring. After stirring overnight the reaction mixture was poured into 5% sodium bicarbonate solution and extracted with ether. The organic phase was washed with 5% HCl and then dried, evaporated, and recrystallized from hexane to give 2.05 g of 6,7-dihydro-5-methylene-3-phenyl-1,2-benzisoxazol-4(5H)-one, m.p. 97°–99° C.

Analysis: Calculated for $C_{14}H_{11}NO_2$: 74.65% C, 4.92% H, 6.22% N. Found: 74.96% C, 5.10% H, 6.21% N.

6,7-Dihydro-5-[(4-methyl-1-piperazinyl)-methyl]-3-phenyl-1,2-benzisoxazol-4(5H)-one dihydrochloride In 5 ml (excess) N-methylpiperazine was added 2.65 g of 6,7-dihydro-5-methylene-3-phenyl-1,2-benzisoxazol-4(5H)-one. The mixture was heated with steam to dissolve the solid completely, then the excess N-methylpiperazine was vacuum distilled off. The residue was dissolved in ether, then dried over $MgSO_4$ and filtered.

The dihydrochloride salt was precipitated from solution by adding excess ethereal HCl. The precipitate was filtered and recrystallized from 7:1 isopropanol/water to yield 3.59 g of 6,7-dihydro-5-[(4-methyl-1-piperazinyl)-methyl]-3-phenyl-1,2-benzisoxazol-4(5H)-one dihydrochloride, m.p. 225° C. (dec).

Analysis: Calculated for $C_{19}H_{23}N_3O_2 \cdot 2HCl$: 57.29% C, 6.33% H, 10.55% N. Found: 57.37% C, 6.35% H, 10.48% N.

EXAMPLE 7 a. 3-Morpholino-2-cyclohexen-1-one

In 700 ml benzene was dissolved 40.0 g 1,3-cyclohexanedione and 62 ml morpholine. The resulting solution was heated at reflux under nitrogen atmosphere for 1.5 hours. The water present in the reaction mixture was collected using a Dean-Stark trap. Upon cooling to room temperature, the reaction mixture was filtered through alumina and the filtrate concentrated in vacuo. Trituration of the resulting oil with ether solidified 62.4 g of 3-morpholino-2-cyclohexen-1-one crystals.

b. 2-Fluorobenzaldehyde oxime

In 200 ml pyridine was dissolved 50.0 g 2-fluorobenzaldehyde and 42.0 g hydroxylamine hydrochloride at room temperature with stirring. The resulting solution was heated on a steam bath for two hours. Upon cooling to room temperature, the reaction mixture was poured into 5% HCl and ether. The layers were separated and the organic phase was washed four times with 5% HCl followed by a final wash with brine. The organic layer was dried ($Na_2SO_4$) filtered and concentrated in vacuo to give 55.0 g of an oil which solidified on standing to yield 2-fluorobenzaldehyde oxime.

c. 2-Fluoro-N-hydroxybenzenecarboximidoyl chloride

In 1 liter dichloromethane was dissolved 55.0 g 2-fluorobenzaldehyde oxime at room temperature with stirring. The resulting solution was cooled to $-10°$ C. and $Cl_2$ was bubbled in at such a rate to maintain temperature below 15° C. After a dark blue color was generated (2-3 minutes) a solution of triethylamine (50 ml) in dichloromethane (100 ml) was added dropwise concurrently with $Cl_2$ addition. When the reaction mixture had maintained a yellow color, additions of the triethylamine solution and $Cl_2$ were discontinued. Concentration of the reaction mixture left an oil which was dissolved in ether and washed four times with 3N HCl followed by a final wash with brine. The organic layer was dried ($MgSO_4$), filtered and concentrated in vacuo to give 60.0 g of 2-fluoro-N-hydroxybenzenecarboximidoyl chloride as an oil which solidified on standing.

d. 6,7-Dihydro-3-(2-fluorophenyl)-1,2-benzisoxazol-4(5H)-one

In 450 ml dichloromethane were combined 62.6 g 3-morpholino-2-cyclohexen-1-one and 96 ml triethylamine at room temperature with stirring. The reaction mixture was kept under nitrogen atmosphere and a solution of 60.0 g 2-fluoro-N-hydroxybenzenecarboximidoyl chloride in 178 ml dichloromethane was added dropwise over five hours. The resulting solution was concentrated in vacuo to an oil which was dissolved in ether and washed three times with 3N HCl followed by a final wash with brine. The organic layer was dried ($MgSO_4$), filtered and concentrated in vacuo to give an oil. Column chromatography on silica (dichloromethane as eluant) gave 20.0 g of an oil which solidified on standing to yield 6,7-dihydro-3-(2-fluorophenyl)-1,2-benzisoxazol-4(5H)-one, m.p. 82°-83° C. after recrystallization from ether-hexane.

Analysis: Calculated for $C_{13}H_{10}FNO_2$: 67.53% C, 4.36% H, 6.06% N. Found: 67.56% C, 4.37% H, 6.01% N.

e. 6,7-Dihydro-5-dimethylaminomethyl-3-(2-fluorophenyl)-1,2-benzisoxazol-4(5H)-one hydrochloride Trifluoroacetic acid (20 ml) was chilled to $-10°$ C. (ice-methanol) and then bisdimethylaminomethane (2.55 g) was added, followed by 6,7-dihydro-3-(2-fluorophenyl)-1,2-benzisoxazol-4(5H)-one (4.60 g). The reaction mixture was warmed at 90° C. for 6 hours and then poured into 5% HCl and washed two times with ether. The aqueous phase was made basic with solid sodium bicarbonate and then extracted with ether. Drying and evaporation gave the product as an oil. The hydrochloride was formed in ethereal HCl and then recrystallized from methanol/ether to give 3.55 g of 6,7-dihydro-5-dimethylaminomethyl-3-(2-fluorophenyl)-1,2-benzisoxazol-4(5H)-one hydrochloride, m.p. 177°-179° C.

Analysis: Calculated for $C_{16}H_{17}FN_2O_2 \cdot HCl$: 59.16% C, 5.59% H, 8.63% N. Found: 59.06% C, 5.65% H, 8.61% N.

EXAMPLE 8

6,7-Dihydro-3-(2-fluorophenyl)-5-[(2-methyl-1H-imidazol-1-yl)-methyl]-1,2-benzisoxazol-4(5H)-one maleate 6,7-Dihydro-5-dimethylaminomethyl-3-(2-fluorophenyl)-1,2-benzisoxazol-4(5H)-one hydrochloride (5.0 g) and 2-methylimidazole (2.65 g) were dissolved in 50 ml of water and the mixture was brought to reflux. After heating for 16 hours the reaction mixture was distributed between $CH_2Cl_2$ and 5% HCl and then the aqueous phase was washed once more with $CH_2Cl_2$. The aqueous phase was then basified with solid sodium bicarbonate and extracted with ether. The organic phase was then dried and evaporated to give the product as an oil. The maleate was formed in methanol/ether and then recrystallized from methanol/ether to give 2.0 g of 6,7-dihydro-3-(2-fluorophenyl)-5-[(2-methyl-1H-imidazol-1-yl)-methyl]-1,2-benzisoxazol-4(5H)-one maleate, m.p. 143°-145° C.

Analysis: Calculated for $C_{18}H_{16}N_3O_2 \cdot C_4H_4O_4$: 59.86% C, 4.56% H, 9.52% N. Found: 59.65% C, 4.54% H, 9.43% N.

EXAMPLE 9

5-(3-Chloropropyl)-6,7-dihydro-3-phenyl-1,2-benzisoxazol-4(5H)-one

In 478 ml anhydrous tetrahydrofuran (THF) was dissolved 10.2 g 6,7-dihydro-3-phenyl-1,2-benzisoxazol-4(5H)-one under nitrogen atmosphere with stirring. The solution was cooled to $-78°$ C. and 47.8 ml lithium diisopropylamide (1.5 molar in cyclohexane) was added dropwise. The resulting solution was stirred for 10 minutes at $-78°$ C. and 7.7 ml 1-chloro-3-iodopropane was added. Upon warming to room temperature, the reaction mixture was poured into water and ether. The layers were separated and the aqueous phase was extracted twice with dichloromethane and twice with ether. The combined organic layers were washed with brine and dried (MgSO$_4$). Filtration and concentration gave the crude product. Column chromatography on silica gel (10% ethyl acetate/hexane) gave 6.2 g of 5-(3-chloropropyl)-6,7-dihydro-3-phenyl-1,2-benzisoxazol-4(5H)-one.

6,7-Dihydro-3-phenyl-5-[3-(1-pyrrolidinyl)-propyl]-1,2-benzisoxazol-4(5H)-one salicylate To a solution consisting of 5-(3-chloropropyl)-6,7-dihydro-3-phenyl-1,2-benzisoxazol-4(5H)-one (3.75 g) and dimethylformamide (37.0 ml) was added diisopropylethyl amine (6.81 ml), pyrrolidine (2.17 ml) and sodium iodide (5.85 g) at room temperature with stirring. The reaction was flushed with nitrogen and warmed at 73°-76° C. for 1.25-2 hours. Upon cooling to room temperature, dilute aqueous sodium bicarbonate and ethyl acetate were added to the reaction mixture. The layers were separated and the aqueous layer extracted twice with ethyl acetate and once with ether. The combined organic layers were washed with brine and dried (MgSO$_4$). Filtration and concentration gave the crude product. Purification via flash column chromatography (silica gel, 2% triethylamine/0-10% methanol/ether) afforded 3.10 g of 6,7-dihydro-3-phenyl-5-[3-(1-pyrrolidinyl)-propyl]-1,2-benzisoxazol-4(5H)-one as an oil which solidified on standing. The salicylate was prepared with 1.07 eq. salicylic acid in ether. The resulting solid was redissolved with methanol. Addition of pentane led to precipitation of the target salt. Filtration and washing with pentane gave 6,7-dihydro-3-phenyl-5-[3-(1-pyrrolidinyl)-propyl]-1,2-benzisoxazol-4(5H)-one salicylate, m.p. 106°-107° C.

Analysis: Calculated for C$_{27}$H$_{30}$N$_2$O$_5$: 70.11% C, 6.54% H, 6.06% N. Found: 70.09% C, 6.54% H, 6.04% N.

EXAMPLE 10

6,7-Dihydro-5-[3-(2-methyl-1H-imidazol-1-yl)-propyl]-3-phenyl-1,2-benzisoxazol-4(5H)-one To a solution consisting of 5-(3-chloropropyl)-6,7-dihydro-3-phenyl-1,2-benzisoxazol-4(5H)-one (5.80 g) and dimethylformamide (57.0 ml) was added 2-methylimidazole (3.30 g), diisopropylethyl amine (10.5 ml) and sodium iodide (9.04 g) at room temperature with stirring. The reaction was flushed with nitrogen and warmed at 76° C. for 1 hour. Upon cooling to room temperature, dilute aqueous sodium bicarbonate and ethyl acetate were added to the reaction mixture. The layers were separated and the aqueous layer extracted twice with ethyl acetate and once with ether. The combined organic layers were washed with brine and concentrated to give the crude product. Drying was accomplished by azeotroping with benzene. Purification via flash column chromatography (silica gel, 2% triethylamine/0-20% methanol/ether) afforded 2.70 g (40%) of 6,7-dihydro-5-[3-(2-methyl-1H-imidazol-1-yl)-propyl]-3-phenyl-1,2-benzisoxazol-4(5H)-one. Recrystallization from dichloromethane/ether/pentane gave the product, m.p. 97°-99° C.

Analysis: Calculated for C$_{20}$H$_{21}$N$_3$O$_2$: 71.62% C, 6.31% H, 12.53% N. Found: 71.46% C, 6.32% H, 12.42% N.

EXAMPLE 11

6,7-Dihydro-5-[3-(4-morpholinyl)-propyl]-3-phenyl-1,2-benzisoxazol-4(5H)-one To a solution consisting of 5-(3-chloropropyl)-6,7-dihydro-3-phenyl-1,2-benzisoxazol-4(5H)-one (5.70 g) and dimethylformamide (56 ml) was added diisopropylethyl amine (8.06 ml), morpholine (3.44 ml) and sodium iodide (8.86 g) at room temperature with stirring. The reaction was flushed with nitrogen and warmed at 78°-80° C. for 2.75-3 hours. Upon cooling to room temperature, water and ethyl acetate were added to the reaction mixture. The layers were separated and the aqueous layer extracted thrice with ethyl acetate and once with ether. The combined organic layers were washed with brine and dried (Na$_2$SO$_4$). Filtration and concentration gave the crude product. Purification via flash column chromatography (silica gel, 2% triethylamine/0-5% methanol/ether) afforded 2.62 g of the product.

Recrystallization from ether/pentane gave 6,7-dihydro-5-[3-(4-morpholinyl)-propyl]-3-phenyl-1,2-benzisoxazol-4(5H)-one, m.p. 86°-88.5° C.

Analysis: Calculated for C$_{20}$H$_{24}$N$_2$O$_3$: 70.57% C, 7.11% H, 8.23% N. Found: 70.47% C, 7.12% H, 8.14% N.

EXAMPLE 12

6,7-Dihydro-5-[3-(4-methyl-1-piperazinyl)-propyl]-3-phenyl-1,2-benzisoxazol-4(5H)-one dihydrochloride To a solution consisting of 5-(3-chloropropyl)-6,7-dihydro-3-phenyl-1,2-benzisoxazol-4(5H)-one (3.90 g) and dimethylformamide (67.0 ml) was added disopropylethyl amine (4.70 ml), 1-methylpiperazine (2.25 ml), and sodium iodide (4.05 g), at room temperature, with stirring. The reaction was flushed with nitrogen and warmed at 96°-98° C. for 2.5-3 hours. Upon cooling to room temperature, dilute aqueous sodium bicarbonate and ethyl acetate were added to the reaction mixture. The layers were separated and the aqueous layer extracted twice with ethyl acetate and once with ether. The combined organic layers were washed with brine and dried (MgSO$_4$). Filtration and concentration gave the crude product. Purification via flash column chromatography (silica gel, 2% triethylamine/5% methanol/ether) afforded 3.07 g of an oil. The dihydrochloride was prepared by dissolving the oil in methanol. Addition of ethereal-HCl led to formation and subsequent precipitation of the salt. Filtration followed by washing with ether and pentane gave 6,7-dihydro-5-[3-(4-methyl-1-piperazinyl)-propyl]-3-phenyl-1,2-benzisoxazol-4(5H)-one dihydrochloride, m.p. 237°-240° C. (dec).

Analysis: Calculated for C$_{21}$H$_{29}$Cl$_2$N$_3$O$_2$: 59.16% C, 6.86% H, 9.85% N. Found: 59.06% C, 6.61% H, 9.81% N.

EXAMPLE 13

6,7-Dihydro-3-phenyl-5-[3-(1-piperidinyl)-propyl]-1,2-benzisoxazol-4(5H)-one To a solution consisting of 5-(3-chloropropyl)-6,7-dihydro-3-phenyl-1,2-benzisoxazol-4(5H)-one (4.00 g) and dimethylformamide (69 ml) was added diisopropylethyl amine (4.81 ml), piperidine (1.50 ml) and sodium iodide (0.62 g) at room temperature with stirring. The reaction was flushed with nitrogen and warmed at 83°–85° C. for 7–8 hours. Upon cooling to room temperature, water and ethyl acetate were added to the reaction mixture. The layers were separated and the aqueous layer extracted twice with ethyl acetate and once with ether. The combined organic layers were washed with brine and dried (MgSO$_4$). Filtration and concentration gave the crude product. Purification via flash column chromatography (silica gel, 2% triethylamine/0–4% methanol/ethyl acetate) afforded 2.30 g of the product. Recrystallization from ether/pentane yielded 6,7-dihydro-3-phenyl-5-[3-(1-piperidinyl)-propyl]-1,2-benzisoxazol-4(5H)-one, m.p. 91.5°–93.5° C.

Analysis: Calculated for C$_{21}$H$_{26}$N$_2$O$_2$: 74.53% C, 7.74% H, 8.28% N. Found: 74.69% C, 7.81% H, 8.25% N.

EXAMPLE 14

6,7-Dihydro-5-[3-(4-(2-methoxyphenyl)-1-piperazinyl)-propyl]-3-phenyl-1,2-benzisoxazol-4(5H)-one dihydrochloride To a solution consisting of 5-(3-chloropropyl)-6,7-dihydro-3-phenyl-1,2-benzisoxazol-4(5H)-one (3.00 g) and dimethylformamide (80 ml) was added diisopropylethyl amine (4.53 ml), 1-(2-methoxyphenyl)piperazine hydrochloride (2.62 g) and sodium iodide (1.6 g) at room temperature with stirring. The reaction was flushed with nitrogen and warmed at 85°–87° C. for 7.5 hours. Upon cooling to room temperature, water and ethyl acetate were added to the reaction mixture. The layers were separated and the aqueous layer extracted three times with ethyl acetate and once with ether. The combined organic layers were washed with brine and dried (K$_2$CO$_3$). Filtration and concentration gave the crude amine product. Purification via flash column chromatography (silica gel, 1% triethylamine/0–0.5% methanol/ether) and another column (alumina, ether) afforded 1.50 g of the amine product. The dihydrochloride was prepared in ether with ethereal HCl. The resulting precipitate was filtered and washed with ether/pentane to yield 6,7-dihydro-5-[3-(4-(2-methoxyphenyl)-1-piperazinyl)-propyl]-3-phenyl-1,2-benzisoxazol-4(5H)-one dihydrochloride, m.p. 182°–185° C.

Analysis: Calculated for C$_{27}$H$_{33}$Cl$_2$N$_3$O$_3$: 62.55% C, 6.42% H, 8.10% N. Found: 62.30% C, 6.39% H, 8.05% N.

EXAMPLE 15

6,7-Dihydro-5-[3-(4-(4-fluorobenzoyl)-1-piperidinyl)-propyl]-3-phenyl-1,2-benzisoxazol-4(5H)-one hydrochloride To a solution consisting of 5-(3-chloropropyl)-6,7-dihydro-3-phenyl-1,2-benzisoxazol-4(5H)-one (6.13 g) and dimethylformamide (DMF) (200 ml) was added diisopropylethyl amine (9.23 ml), 4-(4-fluorobenzoyl)-piperidine hydrochloride (5.67 g) and sodium iodide (3.18 g) at room temperature with stirring. The reaction was flushed with nitrogen and warmed at 85°–87° C. for 7 hours. Upon cooling to room temperature, water and ethyl acetate were added to the reaction mixture. The layers were separated and the aqueous layer extracted three times with ethyl acetate and once with ether. The combined organic layers were washed with brine and dried (K$_2$CO$_3$). Filtration and concentration gave the crude amine product. Purification via flash column chromatography (silica gel, 1% triethylamine (Et$_3$N)/2% methanol/ether), another column (silica gel, 2% Et$_3$N/ether) and another column (alumina, ether) afforded 2.60 g of the amine product as an oil.

The hydrochloride was prepared in ether and methanol with ethereal HCl and pentane. The resulting product was recovered by filtration and washed with pentane to yield 6,7-dihydro-5-[3-(4-(4-fluorobenzoyl)-1-piperidinyl)-propyl]-3-phenyl-1,2-benzisoxazol-4(5H)-one hydrochloride, m.p. 194°–197° C.

Analysis: Calculated for C$_{28}$H$_{30}$ClFN$_2$O$_3$: 67.67% C, 6.08% H, 5.64% N. Found: 67.40% C, 6.05% H, 5.58% N.

EXAMPLE 16

5-[3-(4-(4-Chlorophenyl)-4-hydroxy-piperidinyl)-propyl]-6,7-dihydro-3-phenyl-1,2-benzisoxazol-4(5H)-one To a solution consisting of 5-(3-chloropropyl)-6,7-dihydro-3-phenyl-1,2-benzisoxazol-4(5H)-one (5.02 g) and DMF (170 ml) was added diisopropylethyl amine (7.50 ml), 4-(4-chlorophenyl)-4-hydroxypiperidine (4.03 g) and sodium iodide (2.59 g) at room temperature with stirring. The reaction was flushed with nitrogen and warmed to 78°–80° C. for 11 hours. Upon cooling to room temperature, water and ethyl acetate were added to the reaction mixture. The layers were separated and the aqueous layers extracted three times with ethyl acetate. The combined organic layers were washed with brine and dried (MgSO$_4$). Filtration and concentration gave the crude amine product. Purification via flash chromatography (silica gel, 2% Et$_3$N/ether) afforded 2.60 g of the desired product as an oil. Addition of ether, heat, and slow evaporation gave a powder. The ether was then decanted and the powder was washed with pentane to yield 5-[3-(4-(4-chlorophenyl)-4-hydroxy-piperidinyl)-propyl]-6,7-dihydro-3-phenyl-1,2-benzisoxazol-4(5H)-one, m.p. 147°–148° C.

Analysis: Calculated for C$_{27}$H$_{29}$ClN$_2$O$_3$: 69.74% C, 6.29% H, 6.02% N. Found: 69.75% C, 6.23% H, 5.98% N.

EXAMPLE 17

6,7-Dihydro-5-[3-(4-(2-keto-1-benzimidazolinyl)-1-piperidinyl)-propyl]-3-phenyl-1,2-benzisoxazol-4(5H)-one To a solution consisting of 5-(3-chloropropyl)-6,7-dihydro-3-phenyl-1,2-benzisoxazol-4(5H)-one (4.19 g) and DMF (150 ml) was added diisopropylethyl amine (6.31 ml), 4-(2-keto-1-benzimidazolinyl)piperidine (3.46 g) and sodium iodide (2.17 g) at room temperature with stirring. The reaction was heated at 78° C. under nitrogen atmosphere with stirring (11 hours). Upon cooling to room temperature, water and ethyl acetate were added to the reaction mixture. The layers were separated and the aqueous layer extracted three times with ethyl acetate and once with ether. The combined organic layers were washed with brine and dried (MgSO$_4$). Filtration and concentration gave the crude product. Purification via flash chromatography (silica gel, 1% methanol/2% Et$_3$N/ether) afforded 1.90 g of 6,7-dihydro-5-[3-(4-(2-keto-1-benzimidazolinyl)-1-piperidinyl)-propyl]-3-phenyl-1,2-benzisoxazol-4(5H)-one, m.p. 212°–218° C.

Analysis: Calculated for C$_{28}$H$_{30}$N$_4$O$_3$: 71.47% C, 6.43% H, 11.91% N. Found: 71.25% C, 6.51% H, 11.63% N.

EXAMPLE 18 a.
5-(3-Chloropropyl)-6,7-dihydro-3-(2-fluorophenyl)-1,2-benzisoxazol-4(5H)-one In 500 ml anhydrous THF was dissolved 15.0 g 6,7-dihydro-3-(2-fluorophenyl)-1,2-benzisoxazol-4(5H)-one under nitrogen atmosphere with stirring. The solution was cooled to −78° C. and 65.0 ml lithium diisopropylamide (1.5 molar in cyclohexane) was added dropwise. The resulting solution was stirred for ten minutes at −78° C. and 9.10 ml 1-chloro-3-iodopropane was added. Upon warming to room temperature, the reaction mixture was poured into water and ether. The layers were separated and the aqueous phase was extracted three times with dichloromethane and once with ether. The combined organic layers were washed with brine and dried ($MgSO_4$). Filtration and concentration gave the crude product as an oil. Column chromatography on silica gel (start with 10% dichloromethane in hexane and gradually increase polarity to 100% dichloromethane) gave 5.30 g of 5-(3-chloropropyl)-6,7-dihydro-3-(2-fluorophenyl)-1,2-benzisoxazol-4(5H)-one as an oil.

b.
6,7-Dihydro-3-(2-fluorophenyl)-5-[3-(4-(2-methoxyphenyl)-1-piperazinyl)-propyl]-1,2-benzisoxazol-4(5H)-one dihydrochloride To a solution consisting of 5-(3-chloropropyl)-6,7-dihydro-3-(2-fluorophenyl)-1,2-benzisoxazol-4(5H)-one (5.0 g) and DMF (125 ml) was added diisopropylethyl amine (7.09 ml), 1-(2-methoxyphenyl)piperazine (3.44 g) and sodium iodide (2.44 g) at room temperature with stirring. The reaction was flushed with nitrogen and warmed to 78° C. for 8 hours. Upon cooling to room temperature, water and ethyl acetate were added to the reaction mixture. The layers were separated and the aqueous layer extracted three times with ethyl acetate. The combined organic layers were washed with brine and dried ($MgSO_4$). Filtration and concentration gave the crude amine product. Purification via flash chromatography (silica gel, 1% triethylamine/2% methanol/ether) afforded 1.90 g of the amine product as an oil. The dihydrochloride was prepared in ether with ethereal HCl. Addition of pentane gave a precipitate which was filtered and washed with ether/pentane to yield 6,7-dihydro-3-(2-fluorophenyl)-5-[3-(4-(2-methoxyphenyl)-1-piperazinyl)-propyl]-1,2-benzisoxazol-4(5H)-one dihydrochloride, m.p. 147°-150° C.

Analysis: Calculated for $C_{27}H_{30}FN_3O_3 \cdot 2HCl$: 60.45% C, 6.01% H, 7.83% N. Found: 60.81% C, 6.02% H, 7.89% N.

EXAMPLE 19

6,7-Dihydro-5-[3-(4-(4-fluorobenzoyl)-1-piperidinyl)-propyl]-3-(2-fluorophenyl)-1,2-benzisoxazol-4(5H)-one hydrochloride To a solution consisting of 5-(3-chloropropyl)-6,7-dihydro-3-(2-fluorophenyl)-1,2-benzisoxazol-4(5H)-one (4.24 g) and DMF (125 ml) was added diisopropylethyl amine (6.01 ml), 4-(4-fluorobenzoyl)piperidine hydrochloride (3.69 g) and sodium iodide (2.07 g) at room temperature with stirring. The reaction was flushed with nitrogen and warmed to 78° C. for 8 hours. Upon cooling to room temperature, water, brine and ethyl acetate were added to the reaction mixture. The layers were separated and the aqueous layer extracted four times with ethyl acetate. The combined organic layers were washed with brine and dried ($MgSO_4$). Filtration and concentration gave the crude amine product. Purification via flash chromatography (silica gel, 2% triethylamine ($Et_3N$)/ether) afforded 1.87 g of the amine product as an oil. The hydrochloride was prepared in ether with methanolic HCl. The resultant hydrochloride precipitate was filtered and washed with ether/pentane to yield 6,7-dihydro-5-[3-(4-(4-fluorobenzoyl)-1-piperidinyl)-propyl]-3-(2-fluorophenyl)-1,2-benzisoxazol-4(5H)-one hydrochloride, m.p. 187°-190° C.

Analysis: Calculated for $C_{28}H_{28}F_2N_2O_3 \cdot HCl$: 65.30% C, 5.68% H, 5.44% N. Found: 65.49% C, 5.74% H, 5.44% N.

EXAMPLE 20 a.
5-(3-Chloropropyl)-6,7-dihydro-3-(4-fluorophenyl)-1,2-benzisoxazol-4(5H)-one In a similar manner to that of Examples 7a-d starting with 4-fluorobenzaldehyde oxime, the starting ketone is prepared. In 170 ml anhydrous THF was dissolved 4.0 g 6,7-dihydro-3-(4-fluorophenyl)-1,2-benzisoxazol-4(5H)-one under nitrogen atmosphere with stirring. The solution was cooled to −78° C. and 17.3 ml lithium diisopropylamide (1.50 molar in cyclohexane) was added dropwise. The resulting solution was stirred for ten minutes at −78° C. and 2.2 ml 1-chloro-3-iodopropane was added. Upon warming to room temperature, the reaction mixture was poured into water and the layers were then separated. The aqueous phase was extracted twice with dichloromethane and once with ether. The combined organic layers were washed with brine and dried ($MgSO_4$). Filtration and concentration gave the crude product. Column chromatography on silica gel (start with 10% dichloromethane in hexane and gradually increase polarity to 100% dichloromethane) gave 4.2 g of 5-(3-chloropropyl)-6,7-dihydro-3-(4-fluorophenyl)-1,2-benzisoxazol-4(5H)-one.

b.
6,7-Dihydro-5-[3-(4-(4-fluorobenzoyl)-1-piperidinyl)-propyl]-3-(4-fluorophenyl)-1,2-benzisoxazol-4(5H)-one hydrochloride To a solution consisting of 5-(3-chloropropyl)-6,7-dihydro-3-(4-fluorophenyl)-1,2-benzisoxazol-4(5H)-one (4.2 g) and DMF (120 ml) was added diisopropylethyl amine (7.15 ml), 4-(4-fluorobenzoyl)piperidine hydrochloride (3.98 g) and sodium iodide (2.05 g) at room temperature with stirring. The reaction was flushed with nitrogen and warmed to 80° C. for 12.5 hours. Upon cooling to room temperature, water and ethyl acetate were added to the reaction mixture. The layers were separated and the aqueous layer extracted three times with ethyl acetate. The combined organic layers were washed with brine and dried ($MgSO_4$). Filtration and concentration gave the crude amine product. Purification via flash chromatography (silica gel, 2% $Et_3N$/ether) afforded 2.06 g of the amine as an oil. The hydrochloride was prepared in ether with methanolic HCl. The resultant hydrochloride precipitate was filtered and washed with ether/pentane to yield 6,7-dihydro-5-[3-(4-(4-fluorobenzoyl)-1-piperidinyl)-propyl]-3-(4-fluorophenyl)-1,2-benzisoxazol-4(5H)-one hydrochloride, m.p. 193°-195° C.

Analysis: Calculated for $C_{28}H_{29}ClF_2N_2O_3$ 65.30% C, 5.68% H, 5.44% N. Found: 64.94% C, 5.66% H, 5.39% N.

EXAMPLE 21 a.

3-(4-Chlorophenyl)-5-(3-chloropropyl)-6,7-dihydro-1,2-benzisoxazol-4(5H)-one In a similar manner to that of Examples 7a-d starting with 4-chlorobenzaldehyde oxime, the starting ketone is prepared. In 220 ml anhydrous THF was dissolved 8.1 g 3-(4-chlorophenyl)-6,7-dihydro-1,2-benzisoxazol-4(5H)-one under nitrogen atmosphere with stirring. The solution was cooled to −78° C. and 32.8 ml lithium diisopropylamide (1.5 molar in cyclohexane) was added dropwise. The resulting solution was stirred for fifteen minutes at −78° C. and 4.6 ml 1-chloro-3-iodopropane was added. Upon warming to room temperature, the reaction mixture was poured into water and the layers were separated. The aqueous phase was extracted twice with dichloromethane and once with ether. The combined organic layers were washed with brine and dried (MgSO$_4$). Filtration and concentration gave the crude product. Column chromatography on silica gel (start with 5% dichloromethane in hexane and gradually increase polarity to 100% dichloromethane) gave 5.2 g of 3-(4-chlorophenyl)-5-(3-chloropropyl)-6,7-dihydro-1,2-benzisoxazol-4(5H)-one.

b.

3-(4-Chlorophenyl)-6,7-dihydro-5-[3-(4-(4-fluorobenzoyl)-1-piperidinyl)-propyl]-1,2-benzisoxazol-4(5H)-one To a solution consisting of 3-(4-chlorophenyl)-5-(3-chloropropyl)-6,7-dihydro-1,2-benzisoxazol-4(5H)-one (8.66 g) and DMF (270 ml) was added diisopropylethyl amine (14 ml), 4-(4-fluorobenzoyl)piperidine hydrochloride (7.81 g) and sodium iodide (0.2 g) at room temperature with stirring. The reaction mixture was flushed with nitrogen and warmed to 80° C. for 12 hours. Upon cooling to room temperature, water and ethyl acetate were added to the reaction mixture. The layers were separated and the aqueous layer was extracted three times with ethyl acetate. The combined organic layers were washed with brine and dried (MgSO$_4$). Filtration and concentration gave the crude product. Purification via flash chromatography (silica gel, 2% Et$_3$N/ether) afforded 3.25 g of the product as an oil. Trituration with dry ether solidified the product to yield 3-(4-chlorophenyl)-6,7-dihydro-5-[3-(4-(4-fluorobenzoyl)-1-piperidinyl)-propyl]-1,2-benzisoxazol-4(5H)-one, m.p. 134°–135° C.

Analysis: Calculated for $C_{28}H_{28}ClFN_2O_3$ 67.94% C, 5.70% H, 5.66% N. Found: 67.52% C, 5.66% H, 5.55% N.

EXAMPLE 22

3-(4-Chlorophenyl)-6,7-dihydro-5-[3-(4-(2-methoxyphenyl)-1-piperazinyl)-propyl]-1,2-benzisoxazol-4(5H)-one dihydrochloride To a solution consisting of 3-(4-chlorophenyl)-5-(3-chloropropyl)-6,7-dihydro-1,2-benzisoxazol-4(5H)-one (7.13 g) and DMF (125 ml) was added diisopropylethyl amine (9.6 ml), 1-(2-methoxyphenyl)piperazine (4.24 g) and sodium iodide (0.17 g) at room temperature with stirring. The reaction mixture was flushed with nitrogen and warmed to 80° C. for 10 hours. Upon cooling to room temperature, water and ethyl acetate were added to the reaction mixture. The layers were separated and the aqueous layer extracted three times with ethyl acetate. The combined organic layers were washed with brine and dried (MgSO$_4$). Filtration and concentration gave the crude amine product. Purification via flash chromatography (silica gel, 2% Et$_3$N/ether) afforded 3.31 g of the amine product as an oil. The dihydrochloride was prepared in ether with ethereal HCl. The resultant salt precipitate was filtered and washed with pentane to yield 3-(4-chlorophenyl)-6,7-dihydro-5-[3-(4-(2-methoxyphenyl)-1-piperazinyl)-propyl]-1,2-benzisoxazol-4(5H)-one dihydrochloride, m.p. 208°–210° C.

Analysis: Calculated for $C_{27}H_{32}Cl_3N_3O_3$: 58.65% C, 5.83% H, 7.60% N. Found: 58.93% C, 5.90% H, 7.53% N.

EXAMPLE 23 a.

3-(4-Chlorophenyl)-5-(3-chloropropyl)-4-hydroxy-4,5,6,7-tetrahydro-1,2-benzisoxazole In 100 ml of anhydrous THF was dissolved 6.0 g 3-(4-chlorophenyl)-5-(3-chloropropyl)-1,2-benzisoxazol-4(5H)-one under nitrogen atmosphere. The solution was cooled to −5° C. and 840 mg sodium borohydride was added. The reaction mixture was stirred at 0° C. for 45 minutes and then warmed to 10° C. for 20 minutes. After cooling to 0° C., the reaction mixture was quenched with aqueous NH$_4$Cl (saturated) then extracted with ether. The organic layer was dried (MgSO$_4$), filtered and concentrated in vacuo to give 6.0 g of 3-(4-chlorophenyl)-5-(3-chloropropyl)-4-hydroxy-4,5,6,7-tetrahydro-1,2-benzisoxazole as an oil.

b.

3-(4-Chlorophenyl)-5-[3-(4-(4-fluorobenzoyl)-1-piperidinyl)-propyl]-4-hydroxy-4,5,6,7-tetrahydro-1,2-benzisoxazole To a solution consisting of 3-(4-chlorophenyl)-5-(3-chloropropyl)-4-hydroxy-4,5,6,7-tetrahydro-1,2-benzisoxazole (5.15 g) and DMF (110 ml) was added diisopropylethyl amine (6.0 ml), 4-(4-fluorobenzoyl)piperidine hydrochloride (4.29 g) and sodium iodide (117 mg) at room temperature with stirring. The reaction was flushed with nitrogen and warmed to 80° C. for 12 hours. Upon cooling to room temperature, water and ethyl acetate were added to the reaction mixture. The layers were separated and the aqueous layer was extracted three times with ethyl acetate. The combined organic layers were washed with brine and dried (MgSO$_4$). Filtration and concentration gave the crude product. Purification via flash chromatography (silica gel, 2% Et$_3$N/ether) afforded 1.11 g of the product. Recrystallization from ethyl acetate/ethanol gave 3-(4-chlorophenyl)-5-[3-(4-(4-fluorobenzoyl)-1-piperidinyl)-propyl]-4-hydroxy-4,5,6,7-tetrahydro-1,2-benzisoxazole, m.p. 152°–155° C.

Analysis: Calculated for $C_{28}H_{30}ClFN_2O_3$: 67.67% C, 6.08% H, 5.64% N. Found: 67.31% C, 6.11% H, 5.56% N.

EXAMPLE 24

6,7-Dihydro-3-(4-fluorophenyl)-5-[3-(4-(2-methoxyphenyl)-1-piperazinyl)-propyl]-1,2-benzisoxazol-4(5H)-one To a solution consisting of 5-(3-chloropropyl)-6,7-dihydro-3-(4-fluorophenyl)-1,2-benzisoxazol-4(5H)-one (8.44 g) and DMF (130 ml) was added diisopropylethyl amine (9.6 ml), 1-(2-methoxyphenyl)piperazine (6.87 g) and sodium iodide (0.21 g) at room temperature with stirring. The reaction was flushed with nitrogen and warmed to 80° C. for 12 hours. Upon cooling to room temperature, water and ethyl acetate were added to the reaction mixture. The layers were separated and the aqueous layer was extracted three times with ethyl acetate. The combined organic layers were washed with brine and dried ($MgSO_4$). Filtration and concentration gave the crude amine product. Purification via flash chromatography (silica gel, 2% $Et_3N$/ether) afforded 5.0 g of the amine product as an oil. Trituration with dry ether and pentane solidified the product which was filtered and washed with pentane to yield 6,7-dihydro-3-(4-fluorophenyl)-5-[3-(4-(2-methoxyphenyl)-1-piperazinyl)-propyl]-1,2-benzisoxazol-4(5H)-one, m.p. 107°–108° C.

Analysis: Calculated for $C_{27}H_{30}FN_3O_3$: 69.96% C, 6.52% H, 9.06% N. Found: 70.07% C, 6.57% H, 8.98% N.

EXAMPLE 25

3-(4-Chlorophenyl)-6,7-dihydro-5-[3-(4-(bis-(4-fluorophenyl)methyl)-1-piperazinyl)-propyl]-1,2-benzisoxazol-4(5H)-one To a solution consisting of 3-(4-chlorophenyl)-5-(3-chloropropyl)-6,7-dihydro-1,2-benzisoxazol-4(5H)-one (5.2 g) and DMF (130 ml) was added bis-(4-fluorophenyl)methylpiperazine (6.0 g), diisopropylethyl amine (3.4 ml) and sodium iodide (0.12 g,) at room temperature with stirring. The reaction was flushed with nitrogen and warmed to 80° C. for 12 hours. Upon cooling to room temperature, water and ethyl acetate were added to the reaction mixture. The layers were separated and the aqueous phase extracted three times with ethyl acetate. The combined organic layers were washed with brine and dried ($MgSO_4$). Filtration and concentration gave the crude amine product. Purification via flash chromatography (silica gel, 2% $Et_3N$/ether) afforded 2.6 g of the amine product as an oil. Trituration with dry ether and pentane solidified the product which was filtered and washed with pentane to yield 3-(4-chlorophenyl)-6,7-dihydro-5-[3-(4-fluorophenyl)methyl)-1-piperazinyl)-propyl]-1,2-benzisoxazol-4(5H)-one, m.p. 150°–152° C.

Analysis: Calculated for $C_{33}H_{32}ClF_2N_3O_2$: 68.80% C, 5.60% H, 7.29% N. Found: 68.92% C, 5.73% H, 7.11% N.

EXAMPLE 26 a.

5-(3-Chloropropyl)-6,7-dihydro-3-(3-fluorophenyl)-1,2-benzisoxazol-4(5H)-one

In a similar manner to that of Examples 7a–d starting with 3-fluorobenzaldehyde oxime, the starting ketone is prepared. In 200 ml anhydrous THF was dissolved 11.4 g 6,7-dihydro-3-(3-fluorophenyl)-1,2-benzisoxazol-4(5H)-one under nitrogen atmosphere with stirring. The solution was cooled to −78° C. and 49.4 ml lithium diisopropylamide (1.5 molar in cyclohexane) was added dropwise. The resulting solution was stirred for ten minutes at −78° C. and 6.4 ml 1-chloro-3-iodopropane was added. Upon warming to room temperature, the reaction mixture was poured into water and ether. The layers were separated and the aqueous phase was extracted twice with dichloromethane and once with ether. The combined organic layers were washed with brine and dried ($MgSO_4$). Filtration and concentration gave the crude product. Column chromatography on silica gel (start with 10% dichloromethane in hexane and gradually increase polarity to 100% dichloromethane) gave 4.5 g of 5-(3-chloropropyl)-6,7-dihydro-3-(3-fluorophenyl)-1,2-benzisoxazol-4(5H)-one.

b.

6,7-Dihydro-5-[3-(4-(4-fluorobenzoyl)-1-piperidinyl)-propyl]-3-(3-fluorophenyl)-1,2-benzisoxazol-4(5H)-one hydrochloride To a solution of 5-(3-chloropropyl)-6,7-dihydro-3-(3-fluorophenyl)-2-benzisoxazol-4(5H)-one (4.50 g) and DMF (100 ml) was added anhydrous potassium carbonate (6.10 g), 4-(4-fluorobenzoyl)piperidine hydrochloride (4.30 g) and sodium iodide (0.11 g) at room temperature with stirring. The reaction was flushed with nitrogen and warmed to 80° C. for 12 hours. Upon cooling to room temperature, water and ethyl acetate were added to the reaction mixture. The layers were separated and the aqueous layer was extracted three times with ethyl acetate. The combined organic layers were washed with brine and dried ($MgSO_4$). Filtration and concentration gave the crude amine product. Purification via flash chromatography (silica gel, 2% $Et_3N$/ether) afforded 2.1 g of the amine product as an oil. The hydrochloride was prepared in isopropanol with ethereal HCl. The salt was filtered and washed with pentane to yield 6,7-dihydro-5-[3-(4-(4-fluorobenzoyl)-1-piperidinyl)-propyl]-3-(3-fluorophenyl)-1,2-benzisoxazol-4(5H)-one hydrochloride, m.p. 186°–188° C.

Analysis: Calculated for $C_{28}H_{29}ClF_2N_2O_3$: 65.30% C, 5.68% H, 5.44% N. Found: 65.22% C, 5.75% H, 5.36% N.

EXAMPLE 27 a.

5-(3-Chloropropyl)-6,7-dihydro-3-(4-fluorophenyl)-7-methyl-1,2-benzisoxazol-4(5H)-one In 140 ml anhydrous THF was dissolved 4.20 g 5-(3-chloropropyl)-6,7-dihydro-3-(4-fluorophenyl)-1,2-benzisoxazol-4(5H)-one under nitrogen atmosphere with stirring. The solution was cooled to −78° C. and 14.0 ml lithium diisopropylamide (1.5 molar in cyclohexane) was added dropwise. The resulting solution was stirred for 10 minutes at −78° C. and 1.30 ml iodomethane was added. Upon warming to room temperature, the reaction mixture was poured into water and ether. The layers were separated and the aqueous phase was extracted two times with dichloromethane and once with ether. The combined organic layers were washed with brine and dried ($MgSO_4$). Filtration and concentration gave the crude product as an oil. Column chromatography on silica gel (start eluting with 10% dichloromethane in hexane and gradually increase polarity to 100% dichloromethane) afforded 4.00 g of 5-(3-chloropropyl)-6,7-dihydro-3-(4-fluorophenyl)-7-methyl-1,2-benzisoxazol-4(5H)-one as an oil.

b.

6,7-Dihydro-5-[3-(4-(4-fluorobenzoyl)-1-piperidinyl)-propyl]-3-(4-fluorophenyl)-7-methyl-1,2-benzisoxazol-4(5H)-one hydrochloride To a solution consisting of 5-(3-chloropropyl)-6,7-dihydro-3-(4-fluorophenyl)-7-methyl-1,2-benzisoxazol-4(5H)-one (4.5 g) and DMF (100 ml) was added diisopropylethyl amine (4.9 ml), 4-(4-fluorobenzoyl)piperidine hydrochloride (4.9 g) and sodium iodide (0.10 g), at room temperature with stirring. The reaction was flushed with nitrogen and warmed to 50° C. for 26 hours and then to 80° C. for 6 hours. Upon cooling to room temperature, water and ethyl acetate were added to the reaction mixture. The layers were separated and the aqueous layer extracted three times with ethyl acetate. The combined organic layers were washed with brine and dried (MgSO$_4$). Filtration and concentration gave the crude amine product. Purification via flash chromatography (silica gel, 2% Et$_3$N/ether) afforded 1.9 g of the amine product as an oil. The hydrochloride was prepared in ether with ethereal HCl. Trituration with pentane precipitated the target product. The solid was filtered and washed with pentane to yield 6,7-dihydro-5-[3-(4-(4-fluorobenzoyl)-1-piperidinyl)-propyl]-3-(4-fluorophenyl)-7-methyl-1,2-benzisoxazol-4(5H)-one hydrochloride, m.p. 111°–113° C.

Analysis: Calculated for C$_{29}$H$_{31}$ClF$_2$N$_2$O$_3$: 65.84% C, 5.91% H, 5.30% N. Found: 65.49% C, 6.11% H, 5.11% N.

EXAMPLE 28

6,7-Dihydro-5-[3-(4-(bis-(4-fluorophenyl)methyl)-1-piperazinyl)-propyl]-3-(2-fluorophenyl)-1,2-benzisoxazol-4(5H)-one To a solution consisting of 5-(3-chloropropyl)-6,7-dihydro-3-(2-fluorophenyl)-1,2-benzisoxazol-4(5H)-one (5.3 g) and DMF (100 ml) was added bis-(4-fluorophenyl)methylpiperazine (6.5 g), diisopropylethyl amine (6.0 ml) and sodium iodide (0.13 g) at room temperature with stirring. The reaction was flushed with nitrogen and warmed to 80° C. for 15.5 hours. Upon cooling to room temperature, water and ethyl acetate were added to the reaction mixture. The layers were separated and the aqueous phase extracted three times with ethyl acetate. The combined organic layers were washed with brine and dried (MgSO$_4$). Filtration and concentration gave the crude amine product. Purification via flash chromatography (silica gel, 2% Et$_3$N/ether) afforded 3.8 g of the amine product as an oil. Trituration with dry ether and pentane solidified the product which was filtered and washed with pentane to yield 6,7-dihydro-5-[3-(4-(bis-(4-fluorophenyl)methyl)-1-piperazinyl)-propyl]-3-(2-fluorophenyl)-1,2-benzisoxazol-4(5H)-one, m.p. 95°–97° C.

Analysis: Calculated for C$_{33}$H$_{32}$F$_3$N$_3$O$_2$: 70.83% C, 5.76% H, 7.51% N. Found: 70.84% C, 5.80% H, 7.41% N.

EXAMPLE 29 a.

5-Carbomethoxy-6,7-dihydro-3-(2-fluorophenyl)-1,2-benzisoxazol-4(5H)-one

In a 600 ml anhydrous tetrahydrofuran was dissolved 6,7-dihydro-3-(2-fluorophenyl)-1,2-benzisoxazol-4(5H)-one (20.0 g) under nitrogen. The solution was cooled to −78° C. and 87 ml lithium diisopropylamide was added dropwise. The resulting solution was stirred for ten minutes at −78° C. and 8.7 ml methyl chloroformate was added. Upon warming to room temperature, the reaction mixture was poured into water and ethyl acetate. The layers were separated and the aqueous phase was extracted three times with dichloromethane. The combined organic layers were washed with brine, dried (MgSO$_4$), filtered and concentrated. Column chromatography on silica gel (starting with 10% dichloromethane in hexane and gradually increasing the polarity to 100% DCM) gave 13.5 g of crude product.

b.

5-Carbomethoxy-5-[4-(4-(4-fluorobenzoyl)-1-piperidinyl)-butyl)]-3-(2-fluorophenyl)-6,7-dihydro-1,2-benzisoxazol-4(5H)-one oxalate To a solution consisting of 5-carbomethoxy-3-(2-fluorophenyl)6,7-dihydro-1,2-benzisoxazol-4(5H)-one (7.0 g,) and acetone (60 ml) was added potassium carbonate (13.4 g), 1-bromo-4-chlorobutane (3.6 ml) and sodium iodide (360 mg) at room temperature with stirring. The reaction mixture was heated to reflux for 6 hours. Upon cooling to room temperature water and ethyl acetate were added to the reaction mixture. The layers were separated and the aqueous phase was extracted three times with ethyl acetate. The combined organic layers were washed with brine and dried (MgSO$_4$). Filtration and concentration gave the crude product. Purification via preparative HPLC (silica gel, 20% ethyl acetate/hexane) afforded 7.3 g of the product 5-carbomethoxy-5-(4-chlorobutyl)-3-(2-fluorophenyl)-6,7-dihydro-1,2-benzisoxazol-4(5H)-one.

To a solution consisting of the above product (7.3 g) in DMF (100 ml) was added 4-(4-fluorobenzoyl)piperidine (5.2 g), potassium carbonate (3.5 g) and sodium iodide (140 mg) at room temperature with stirring. The flask was flushed with nitrogen and warmed to 80° C. for 10 hours. Upon cooling to room temperature, water and ethyl acetate were added to the reaction mixture. The layers were separated and the aqueous phase was extracted three times with ethyl acetate. The combined organic layers were washed with brine and dried (MgSO$_4$). Filtration and concentration gave the crude product. Purification via flash column chromatography (silica gel, 2% triethylamine/ether) afforded 3.6 g of an oil. The oxalate salt was prepared in ethanol. The resultant precipitate was filtered and washed with ether/pentant to yield 5-carbamethoxy-5-[4-(4-(4-fluorobenzoyl)-1-piperidinyl)-butyl]-3-(2-fluorophenyl)-6,7-dihydro-1,2-benzisoxazol-4(5H)-one oxalate as an oil. The oxalate salt was prepared in ethanol. The precipiate was filtered and washed with ether/pentane, m.p. 208°–210° C. The oxalate salt was prepared in ethanol. The precipiate was filtered and washed with ether/pentane, m.p. 208°–210° C.

Analysis: Calculated for C$_{33}$H$_{34}$F$_2$N$_2$O$_9$: 61.87% C, 5.35% H, 4.37% N. Found: 61.64% C, 5.09% H, 4.28% N.

EXAMPLE 30

5-[3-[4-(6-Fluoro-1,2-benzisoxazol-3-yl)-1-piperidinyl]-propyl]-3-(2-fluorophenyl)-6,7-dihydro-1,2-benzisoxazol-4(5H)-one oxalate To a solution consisting of 5-(3-chloropropyl)-6,7-dihydro-3-(2-fluorophenyl)-1,2-benzisozaxol-4(5H)-one (3.4 g) and DMF (100 ml) was added 6-fluoro-3-(4-piperidinyl)-1,2-benzisoxazole (3.2 g), diisopropylethyl amine (3.9 ml), and sodium iodide (83 mg) at room temperature with stirring. The flask was flushed with nitrogen and warmed at 80° C. for 17 hours. Upon cooling to room temperature, water and ethyl acetate were added to the reaction mixture. The layers were separated and the aqueous phase extracted 3 times with ethyl acetate. The combined organic layers were washed with brine and dried (MgSO$_4$). Filtration and concentration gave the crude product. Purification via flash column chromatography (silica gel, 2% triethylamine) afforded 2.4 g of 5-[3-[4-(6-fluoro-1,2-benzisoxazol-3-yl)-1-piperidinyl]propyl]-3-(2-fluorophenyl)-6,7-dihydro-1,2-benzisoxazol-4-(5H)-one, as an oil. The oxalate salt was prepared in ethanol with oxalic acid. The precipitate was filtered and washed with ether/pentane, m.p. 201°-203° C.

Analysis: Calculated for $C_{30}H_{29}F_2N_3O_7$: 61.96% C, 5.03% H, 7.23% N. Found: 61.80% C, 4.89% H, 7.20% N.

EXAMPLE 31 a.

4,5,6,7-Tetrahydro-4-oxo-3-phenyl-1,2-benzisoxazol-5-acetic acid ethyl ester

In 115 ml anhydrous tetrahydrofuran was dissolved 2.44 g of 6,7-dihydro-3-phenyl-1,2-benzisoxazol-4(5H)-one under nitrogen. The solution was cooled to −78° C. and 11.5 ml lithium diisopropylamide was added dropwise. The resultant solution was stirred for 15 minutes at −78° C. and ethyl bromoacetate (2.6 ml) was added. Upon warming to room temperature, the reaction mixture was poured into water and ether. The layers were separated and the aqueous phase was extracted three times with dichloromethane and once with ether. The combined organic layers were washed with brine and dried (MgSO$_4$). Flash column chromatography (30% ethyl acetate/hexane) gave 2.94 g of 4,5,6,7-tetrahydro-4-oxo-3-phenyl-1,2-benzisoxazol-5-acetic acid ethyl ester b.

4-Hydroxy-5-(2-hydroxyethyl)-3-phenyl-4,5,6,7-tetrahydro-1,2-benzisoxazole

In a 2 liter round-bottomed flask was dissolved 4,5,6,7-dihydro-4-oxo-3-phenyl-1,2-benzisoxazol-5-acetic acid ethyl ester (3.0 g) in absolute ethanol (300 ml) at room temperature. Sodium borohydride (6.07 g) was added and the solution was heated to reflux. The solution was cooled to room temperature, then diluted with saturated NH$_4$Cl until a solid appeared. The reaction mixture was basified to pH 9 using 10% NaOH (aq.). The product, an oil, was extracted with ether and the aqueous phase was extracted twice with ether. The combined organic layers were washed with brine, dried (MgSO$_4$), filtered and concentrated to give 2.60 g of 4-hydroxy-5-(2-hydroxyethyl)-3-phenyl-4,5,6,7-tetrahydro-1,2-benzisoxazole.

c.

3-Phenyl-5-(2-tosyloxyethyl)-4-hydroxy-4,5,6,7-tetrahydro-1,2-benzisoxazole

In 30 ml pyridine was dissolved 4-hydroxy-5-(2-hydroxyethyl)-3-phenyl-4,5,6,7-tetrahydro-1,2-benzisoxazole (2.1 g) and the mixture was cooled to 0° C. Tosyl chloride (1.54 g) was added and the solution was stirred at 0° C. for 30 minutes. The reaction mixture was poured into ice water, then extracted four times with ether. The mixture was dried (Na$_2$SO$_4$) and then concentrated at room temperature to yield 2.67 g of 3-phenyl-5-(2-tosyloxyethyl)-4-hydroxy-4,5,6,7-tetrahydro-1,2-benzisoxazole.

d.

5-[2-(4-(4-Fluorobenzoyl)-1-piperidinyl)-ethyl]-3-phenyl-6,7-dihydro-1,2-benzisoxazol-4(5H)-one hydrochloride To a solution consisting of 3-phenyl-5-(2-tosyloxyethyl)-4-hydroxy-4,5,6,7-tetrahydro-1,2-benzisoxazole (8.0 g) and DMF (100 ml) was added diisopropylethyl amine (6.7 ml) and 4-(4-fluorobenzoyl)piperidine hydrochloride (7.1 g) at room temperature with stirring. The flask was flushed with nitrogen and warmed to 80° C. for 4.5 hours. Upon cooling to room temperature, water and ethyl acetate were added to the reaction mixture. The layers were separated and the aqueous phase was extracted 3 times with ethyl acetate. The combined organic layers were washed with brine and dried (MgSO$_4$). Filtration and concentration gave the crude product. Purification via flash column chromatography (silica gel, 2% triethylamine/ether) afforded 1.3 g of 5-[2-(4-(4-fluorobenzoyl)-1-piperidinyl)-ethyl]-3-phenyl-4-hydroxy-4,5,6,7-tetrahydro-1,2-benzisoxazole.

To a solution of the above product (1.3 g) in DMF (25 ml) was added a solution of pyridinium dichromate (1.9 g) in DMF (10 ml). The flask was flushed with nitrogen and allowed to stir at room temperature for 17 hours under nitrogen atmosphere. The reaction mixture was poured into water and ethyl acetate. The layers were separated and the aqueous phase was extracted 4 times with ethyl acetate. The combined organic layers were washed with brine and dried (MgSO$_4$). Filtration and concentration gave the crude product. Purification via flash column chromatography (silica gel, 2% triethylamine/ether) afforded 0.8 g of 5-[2-(4-(4-fluorobenzoyl)-1-piperidinyl)-ethyl]-3-phenyl-6,7-dihydro-1,2-benzisoxazol-4(5H)-one. The colored impurities were removed by flushing the product thru alumina with ether. The hydrochloride salt was prepared in isopropanol with ethereal HCl. The precipitate was filtered and washed with pentane, m.p. 211°-215° C.

Analysis: Calculated for $C_{27}H_{28}ClFN_2O_3$: 67.14% C, 5.84% H, 5.80% N. Found: 67.31% C, 6.03% H, 5.70% N.

EXAMPLE 32

5-[2-(4-(4-Fluorobenzoyl)-1-piperidinyl)-ethyl]-3-(2-fluorphenyl)-6,7-dihydro-1,2-benzisoxazol-4(5H)-one salicylate To a solution consisting of 5-(2-chloroethyl)-3-(2-fluorophenyl)-6,7-dihydro-1,2-benzisoxazol-4(5H)-one (2.5 g) and DMF (85 ml) was added anhydrous potassium carbonate (0.6 g), diisopropylethyl amine (2.2 ml), 4-(4-fluorobenzoyl)piperidine (2.3 g) and potassium iodide (70 mg) at room temperature with stirring. The flask was flushed with nitrogen and warmed to 80° C. for 19 hours. Upon cooling to room temperature, water and ethyl acetate were added to the reaction mixture. The layers were separated and the aqueous phase was extracted 3 times with ethyl acetate. The combined organic layers were washed with brine and dried (MgSO$_4$). Filtration and concentration gave the crude product.

Purification via flash column chromatography (silica gel, 2% triethylamine/ether) afforded 1.5 g of 5-[2-(4-(4-fluorobenzoyl)-1-piperidinyl)-ethyl]-3-(2-fluorphenyl)-6,7-dihydro-1,2-benzisoxazol-4-(5H)-one, as an oil. The product was flushed thru alumina with ether.

The salicylate was prepared in ether and the resulting salt was washed with ether/pentane, m.p. 80°-82° C.

Analysis: Calculated for $C_{34}H_{32}F_2N_2O_6$: 67.76% C, 5.35% H, 4.65% N. Found: 67.26% C, 5.31% H, 4.78% N.

EXAMPLE 33

5-[3-[4-(1,2-Benzisothiazol-3-yl)-1-piperazinyl]propyl]-3-(2-fluorophenyl)-6,7-dihydro-1,2-benzisoxazol-4(5H)-one hydrochloride To a solution consisting of 5-(3-chloropropyl)-3-(2-fluorophenyl)-6,7-dihydro-1,2-benzisoxazol-4(5H)-one (1.36 g) and DMF (40 ml) was added anhydrous potassium carbonate (0.3 g), diisopropylethyl amine (0.8 ml), 3-piperazinyl-1,2-benzisothiazol (1.26 g) and potassium iodide (27 mg) at room temperature with stirring. The flask was flushed with nitrogen and warmed to 80° C. for 12 hours. Upon cooling to room temperature, water and ethyl acetate were added to the reaction mixture. The layers were separated and the aqueous phase was extracted three times with ethyl acetate. The combined organic layers were washed with brine and dried (MgSO₄). Filtration and concentration gave the crude product. Purification via flash column chromatography (silica gel, 20% triethylamine/ether) afforded 1.0 g of 5-[3-[4-(1,2-benzisothiazol-3-yl)-1-piperazinyl]propyl]-3-(2-fluorophenyl)-6,7-dihydro-1,2-benzisoxazol-4(5H)-one as a foam. The product was flushed through alumina with dichloromethane. The hydrochloride was prepared by dissolving the free amine with menthanol and adding ethereal HCl. The salt was filtered and washed with pentane, m.p. 215° C. (dec.).

Analysis: Calculated for $C_{27}H_{28}ClFN_4O_2S$: 61.53% C, 5.35% H, 10.63% N. Found: 61.12% C, 5.34% H, 10.52% N.

EXAMPLE 34

6,7-Dihydro-5-[3-(4-(4-fluorophenyl)-1-piperazinyl)-propyl]-3-(2-fluorophenyl)-1,2-benzisoxazol-4(5H)-one hydrochloride monohydrate To a solution consisting of 5-(3-chloropropyl)-3-(2-fluorophenyl)-6,7-dihydro-1,2-benzisoxazol-4(5H)-one (5.8 g) and DMF (100 ml) was added anhydrous potassium carbonate (1.3 g), diisopropylethyl amine (4.9 ml), 1-(4-fluorophenyl)piperazine (4.1 g) and potassium iodide (0.3 g) at room temperature with stirring. The flask was flushed with nitrogen and warmed to 80° C. for 13.5 hours. Upon cooling to room temperature, water and ethyl acetate were added to the reaction mixture. The layers were separated and the aqueous phase was extracted 3 times with ethyl acetate. The combined organic layers were washed with water twice, brine, and then dried (MgSO₄). Filtration and concentration gave the crude product. Purification via flash column chromatography (silica gel, 2% triethylamine/ether) afforded 4.0 g of 6,7-dihydro-5-[3-(4-(4-fluorophenyl)-1-piperazinyl)-propyl]-3-(2-fluorophenyl)-1,2-benzisoxazol-4(5H)-one as an oil. The product was flushed thru alumina with ether. The hydrochloride was prepared in ether with ethereal HCl. The precipitate was filtered and washed with pentane, m.p. 161°-164° C.

Analysis: Calculated for $C_{26}H_{30}ClF_2N_3O_3$: 61.72% C, 5.98% H, 8.30% N. Found: 61.70% C, 5.64% H, 8.27% N.

EXAMPLE 35

6,7-Dihydro-3-(2-fluorophenyl)-5-[3-(4-(2-pyridyl)-1-piperazinyl)-propyl]-1,2-benzisoxazol-4(5H)-one To a solution consisting of 5-(3-chloropropyl)-3-(2-fluorophenyl)-6,7-dihydro-1,2-benzisoxazol-4(5H)-one (6.4 g) and DMF (100 ml) was added anhydrous potassium carbonate (1.4 g), diisopropylethyl amine (5.4 ml), 1-(2-pyridyl)piperazine (4.8 ml) and potassium iodide (0.4 g) at room temperature with stirring. The flask was flushed with nitrogen and warmed to 80° C. for 16 hours. Upon cooling to room temperature, water and ethyl acetate were added to the reaction mixture. The layers were separated and the aqueous phase was extracted three times with ethyl acetate. The combined organic layers were washed with water twice, then brine and dried (MgSO₄). Filtration and concentration gave the crude product. Purification via preparative HPLC (silica gel, 3% methanol) afforded 4.2 g of 6,7-dihydro-3-(2-fluorophenyl)-5-[3-(4-(2-pyridyl)-1-piperazinyl)-propyl]-1,2-benzisoxazol-4(5H)-one, as an oil which solidified upon standing. The product was recrystallized from ether, m.p. 94°-96° C.

Analysis: Calculated for $C_{25}H_{27}FN_4O_2$: 69.11% C, 6.26% H, 12.89% N. Found: 68.88% C, 6.25% H, 12.84% N.

EXAMPLE 36

5-[3-(4-(3-Chlorophenyl)-1-piperazinyl)-propyl]-6,7-dihydro-3-(2-fluorophenyl)-1,2-benzisoxazol-4(5H)-one hydrochloride To a solution consisting of 5-(3-chloropropyl)-3-(2-fluorophenyl)-6,7-dihydro-1,2-benzisoxazol-4(5H)-one (6.0 g) and DMF (100 ml) was added anhydrous potassium carbonate (1.4 g), diisopropylethylamine (5.1 ml), 1-(3-chlorophenyl)piperazine (4.9 g) and potassium iodide (0.3 g) at room temperature with stirring. The flask was flushed with nitrogen and warmed to 80° C. for 18 hours. Upon cooling to room temperature, water and ethyl acetate were added to the reaction mixture. The layers were separated and the aqueous phase was extracted 3 times with ethyl acetate. The combined organic layers were washed with water twice, then brine twice, and dried (MgSO₄). Filtration and concentration gave the crude product. Purification via flash column chromatography (silica gel) afforded 3.4 g of 5-[3-(4-(3-chlorophenyl)-1-piperazinyl)propyl]-6,7-dihydro-3-(2-fluorophenyl)-1,2-benzisoxazol-4(5H)-one as an oil. The hydrochloride was prepared in methanol with ethereal HCl. The precipitate was filtered and washed with anhydrous ether, m.p. 104°-106° C.

Analysis: Calculated for $C_{26}H_{28}Cl_2FN_3O_2$: 61.91% C, 5.59% H, 8.33% N. Found: 61.75% C, 5.63% H, 8.30% N.

EXAMPLE 37

6,7-Dihydro-3-(2-fluorophenyl)-5-[3-(4-(2-pyrimidyl)-1-piperazinyl)-propyl]-1,2-benzisoxazol-4(5H)-one To a solution consisting of 5-(3-chloropropyl)-3-(2-fluorophenyl)-6,7-dihydro-1,2-benzisoxazol-4(5H)-one (7.3 g) and DMF (100 ml) was added anhydrous potassium carbonate (1.6 g), diisopropylethyl amine (6.2 ml), 1-(2-pyrimidyl)piperazine (5.8 g) and potassium iodide (0.4 g) at room temperature with stirring. The flask was flushed with nitrogen and warmed to 80° C. for 16 hours. Upon cooling to room temperature, water and ethyl acetate were added to the reaction mixture. The layers were separated and the aqueous phase was extracted 3 times with ethyl acetate. The combined organic layers were washed with water twice, then brine and dried (MgSO$_4$). Filtration and concentration gave the crude product. Purification via flash column chromatography (silica gel, 2% triethylamine/ether) afforded 4.0 g of 6,7-dihydro-3-(2-fluorophenyl)-5-[3-(4-(2-pyrimidyl)-1-piperazinyl)-propyl]-1,2-benzisoxazol-4(5H)-one as an oil which solidified upon standing. Recrystallization with ether gave the product as a solid, m.p. 115°-117° C.

Analysis: Calculated for C$_{24}$H$_{26}$FN$_5$O$_2$: 66.19% C, 6.02% H, 16.08% N. Found: 65.96% C, 5.88% H, 15.94% N.

EXAMPLE 38

6,7-Dihydro-5-(4-(4-fluorobenzoyl)-1-piperidinyl)methyl-3-(2-fluorophenyl)-1,2-benzisoxazol-4(5H)-one To a solution consisting of 6,7-dihydro-5-dimethylaminomethyl-3-(2-fluorophenyl)-1,2-benzisoxazol-4(5H)-one hydrochloride (1.86 g) in distilled water (18.5 ml) was added 4-(4-fluorobenzoyl)piperidine hydrochloride (2.78 g) and potassium carbonate (0.80 g). The reaction mixture was heated at reflux for 3 hours. Upon cooling to room temperature, ethyl acetate was added and the layers were separated. The aqueous phase was extracted twice with ethyl acetate. The combined organic layers were washed with brine and dried (MgSO$_4$). Filtration and concentration gave the crude product. Purification via flash column chromatography (silica gel, 40% ethyl acetate/hexane) afforded 1.20 g of 6,7-dihydro-5-(4-(4-fluorobenzoyl)-1-piperidinyl)methyl-3-(2-fluorophenyl)-1,2-benzisoxazol-4(5H)-one. The compound was flushed through alumina with dichloromethane to give an oil which solidified on standing. The product was then recrystallized from ether/hexane, m.p. 99°-102° C.

Analysis: Calculated for C$_{26}$H$_{24}$F$_2$N$_2$O$_3$: 69.32% C, 5.37% H, 6.22% N. Found: 69.41% C, 5.52% H, 6.20% N.

EXAMPLE 39

6,7-Dihydro-3-(2-fluorophenyl)-5-[(4-(2-methoxyphenyl)-1-piperazinyl)methyl]-1,2-benzisoxazol-4(5H)-one maleate To a solution consisting of 6,7-dihydro-5-dimethylaminomethyl-3-(2-fluorophenyl)-1,2-benzisoxazol-4(5H)-one hydrochloride (2.40 g) in distilled water (24 ml) was added 1-(2-methoxyphenyl)piperazine hydrochloride (3.38 g) and potassium carbonate (1.02 g) at room temperature with stirring. The resulting reaction mixture was heated to reflux for 25 min. and allowed to cool to room temperature. Diethyl ether was then added and the layers separated. The aqueous phase was extracted twice with ether. The combined organics were washed with brine and dried (Na$_2$SO$_4$). Filtration and concentration gave the crude product. Purification via flash column chromatography (silica gel, ether) afforded 2.45 g of 6,7-dihydro-3-(2-fluorophenyl)-5-(4-(2-methoxyphenyl)-1-piperazinyl)methyl-1,2-benzisoxazol-4(5H)-one as a foam. The compound was flushed thru alumina with dichloromethane to give an oil. The maleate was prepared in ethanol and the resulting salt was washed with ether, m.p. 153°-155° C.

Analysis: Calculated for C$_{29}$H$_{30}$FN$_3$O$_7$: 63.15% C, 5.48% H, 7.62% N. Found: 63.04% C, 5.53% H, 7.56% N.

EXAMPLE 40 a.

5-(3-Chloropropyl)-6,7-dihydro-3-methyl-1,2-benzisoxazol-4(5H)-one

In 100 ml anhydous THF was dissolved 6,7-dihydro-3-methyl-1,2-benzisoxazol-4(5H)-one (2.2 g) under nitrogen. The solution was cooled to 0° C. and 10.2 ml lithium diisopropylamide was added dropwise. The solution was stirred at 0° C. for 2.5 hours and quenched with 1-chloro-3-iodopropane (1.6 ml). The solution was removed from the ice bath and warmed to 40° C. under nitrogen. Upon cooling to room temperature, the reaction mixture was poured into water and ether. The layers were separated and the aqueous phase was extracted three times with dichloromethane and once with ether. The combined organic layers were washed once with water and salt brine, dried (MgSO$_4$), filtered and concentrated. Flash column chromatography on silica gel (15% ethyl acetate/hexane) gave 850 mg of 5-(3-chloropropyl)-6,7-dihydro-3-methyl-1,2-benzisoxazol-4(5H)-one.

b.

6,7-Dihydro-5-[3-(4-(4-fluorobenzoyl)-1-piperidinyl)-propyl]-3-methyl-1,2-benzisoxazol-4(5H)-one To a solution consisting of 5-(3-chloropropyl)-6,7-dihydro-3-methyl-1,2-benzisoxazol-4(5H)-one (0.85 g) and DMF (20 ml) was added anhydrous potassium carbonate (0.52 g) diisopropylethyl amine (0.33 ml), 4-(4-fluorobenzoyl)piperidine (0.92 g) and potassium iodide (62 mg) at room temperature with stirring. The flask was flushed with nitrogen and warmed to 80° C. for 24 hours. Upon cooling to room temperature, water and ethyl acetate were added to the reaction mixture. The layers were separated and the aqueous phase was extracted 3 times with ethyl acetate. The combined organic layers were washed with water twice, then brine. The organic phase was then dried (MgSO$_4$), filtered, and concentrated to give the crude product. Purification via flash column chromatography (silica gel, 2% triethylamine/ether) afforded 0.70 g of 6,7-dihydro-5-[3-(4-(4-fluorobenzoyl)-1-piperidinyl)-propyl]-3-methyl-1,2-benzisoxazol-4(5H)-one as an oil which solidified on standing. The product was dissolved and flushed through alumina with dichloromethane. Recrystallization with ether/hexane gave the product as a solid, m.p. 81°-83° C.

Analysis: Calculated for C$_{23}$H$_{27}$FN$_2$O$_3$: 69.33% C, 6.83% H, 7.03% N. Found: 69.51% C, 6.65% H, 7.01% N.

We claim:

1. A compound of the formula

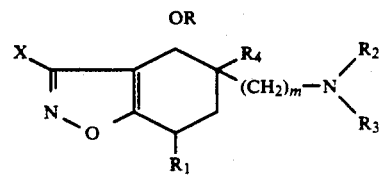

wherein X is

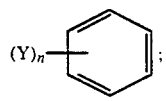

Y is hydrogen, halogen, loweralkyl, loweralkoxy, trifluoromethyl, nitro or amino; R is H when the bond between the oxygen atom and the carbon atom in question is a single bond; otherwise the dotted line signifies part of a double bond to the oxygen atom; $R_1$ is hydrogen, loweralkyl or arylloweralkyl; $R_2$ and $R_3$ are independently hydrogen, loweralkyl or arylloweralkyl, or $R_2$ and $R_3$ taken together with the nitrogen atom form an optionally substituted heterocycle selected from the group consisting of piperidinyl, pyrrolidinyl, morpholinyl, imidazol-1-yl, 1-piperazinyl, said substituents being hydrogen or loweralkyl; 4-substituted-1-piperazinyl of the formula

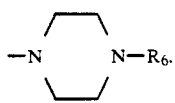

where $R_6$ is aryl, arylloweralkyl,

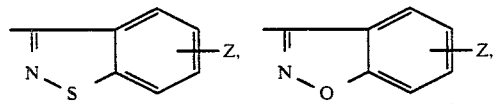

2-pyrimidyl,

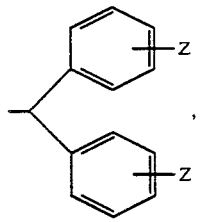

2-pyridinyl of the formula

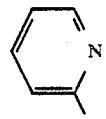

or 4-pyridinyl of the formula

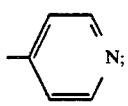

4-substituted-1-piperidinyl of the formula

wherein $R_7$ is hydrogen, loweralkyl, aryl, arylloweralkyl, 2-pyridinyl of the formula

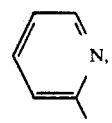

4-pyridinyl of the formula

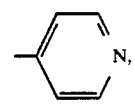

2-pyrimidinyl of the formula

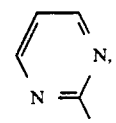

arylcarbonyl,

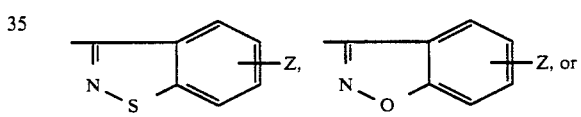

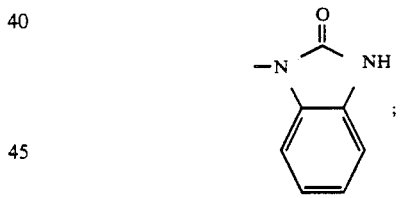

$R_8$ is hydrogen or —OH; with the proviso that $R_7$ and $R_8$ are not simultaneously hydrogen and that $R_7$ is not loweralkyl when $R_8$ is hydrogen, $R_4$ is hydrogen, loweralkoxycarbonyl or aryloxycarbonyl; Z is chlorine, bromine or fluorine; m is an integer of 1 to 4; n is an integer of 1 to 4 or a pharmaceutically acceptable acid addition salt thereof and where applicable the geometric and optical isomers and racemic mixtures thereof.

2. The compound as defined in claim 1 wherein X is

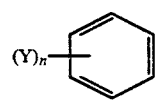

and Y is hydrogen or halogen; R is hydrogen; $R_1$ is hydrogen or loweralkyl; $R_2$ and $R_3$ are loweralkyl or $R_2$ and $R_3$ taken together with the nitrogen is a heterocycle selected from the group consisting of piperidinyl, pyrrolidinyl, morpholinyl and 4-piperazinyl; and m is 1, 2 or 3.

3. The compound as defined in claim 2 wherein Y is fluorine, $R_1$ is hydrogen or methyl, $R_2$ and $R_3$ taken together with the nitrogen is a heterocycle selected from piperidinyl or 4-piperazinyl and m is 3.

4. The compound as defined in claim 1 which is 6,7-dihydro-5-(4-morpholinylmethyl)-3-phenyl-1,2-benzisoxazol-4(5H)-one.

5. The compound as defined in claim 1 which is 6,7-dihydro-5-[3-(4-morpholinyl)-propyl]-3-phenyl-1,2-benzisoxazol-4(5H)-one.

6. The compound as defined in claim 1 which is 6,7-dihydro-5-dimethylaminomethyl-3-phenyl-1,2-benzisoxazol-4(5H)-one.

7. The compound as defined in claim 1 which is 5-(dimethylaminomethyl)-4-hydroxy-3-phenyl-4,5,6,7-tetrahydro-1,2-benzisoxazole.

8. The compound as defined in claim 7 wherein said compound is the cis isomer.

9. The compound as defined in claim 7 wherein said compound is the trans isomer.

10. The compound as defined in claim 1 which is 6,7-dihydro-5-dimethylaminomethyl-3-(2-fluorophenyl)-1,2-benzisoxazol-4(5H)-one.

11. The compound as defined in claim 1 which is 6,7-dihydro-5-[3-(2-methyl-1H-imidazol-1-yl)-propyl]-3-phenyl-1,2-benzisoxazol-4(5H)-one.

12. The compound as defined in claim 1 which is 6,7-dihydro-5-[(2-methyl-1H-imidazol-1-yl)methyl]-3-(2-fluorophenyl)-1,2-benzisoxazol-4(5H)-one.

13. The compound as defined in claim 1 which is 6,7-dihydro-3-phenyl-5-[3-(1-pyrrolidinyl)-propyl]-1,2-benzisoxazol-4-(5H)-one.

14. The compound as defined in claim 1 which is 6,7-dihydro-5-(1-piperidinylmethyl)-3-phenyl-1,2-benzisoxazol-4(5H)-one.

15. The compound as defined in claim 1 which is 6,7-dihydro-3-phenyl-5-[3-(1-piperidinyl)-propyl]-1,2-benzisoxazol-4(5H)-one.

16. The compound as defined in claim 1 which is 6,7-dihydro-5-[3-(4-(4-fluorobenzoyl)-1-piperidinyl)-propyl]-3-phenyl-1,2-benzisoxazol-4(5H)-one.

17. The compound as defined in claim 1 which is 5-[3-(4-(4-chlorophenyl)-4-hydroxy-1-piperidinyl)-propyl]-6,7-dihydro-3-phenyl-1,2-benzisoxazol-4(5H)-one.

18. The compound as defined in claim 1 which is 6,7-dihydro-5-[3-(4-(2-keto-1-benzimidazolinyl)-1-piperidinyl)-propyl]-3-phenyl-1,2-benzisoxazol-4(5H)-one.

19. The compound as defined in claim 1 which is 6,7-dihydro-5-[3-(4-(4-fluorobenzoyl)-1-piperidinyl)-propyl]-3-(2-fluorophenyl)-1,2-benzisoxazol-4(5H)-one.

20. The compound as defined in claim 1 which is 6,7-dihydro-5-[3-(4-(4-fluorobenzoyl)-1-piperidinyl)-propyl]-3-(4-fluorophenyl)-1,2-benzisoxazol-4(5H)-one.

21. The compound as defined in claim 1 which is 3-(4-chlorophenyl)-6,7-dihydro-5-[3-(4-(4-fluorobenzoyl)-1-piperidinyl)-propyl]-1,2-benzisoxazol-4(5H)-one.

22. The compound as defined in claim 1 which is 3-(4-chlorophenyl)-5-[3-(4-(4-fluorobenzoyl)-1-piperidinyl)-propyl]-4-hydroxy-4,5,6,7-tetrahydro-1,2-benzisoxazole.

23. The compound as defined in claim 1 which is 6,7-dihydro-5-[3-(4-(4-fluorophenyl)-1-piperidinyl)-propyl]-3-(3-fluorophenyl)-1,2-benzisoxazol-4(5H)-one.

24. The compound as defined in claim 1 which is 6,7-dihydro-5-[3-(4-(4-fluorobenzoyl)-1-piperidinyl)-propyl]-3-(4-fluorophenyl)-7-methyl-1,2-benzisoxazol-4(5H)-one.

25. The compound as defined in claim 1 which is 5-carbomethoxy-5-[4-(4-(4-fluorobenzoyl)-1-piperidinyl)-butyl]-3-(2-fluorophenyl)-6,7-dihydro-1,2-benzisoxazol-4(5H)-one.

26. The compound as defined in claim 1 which is 5-[3-[4-(6-fluoro-1,2-benzisoxazol-3-yl)-1-piperidinyl]-propyl]-3-(2-fluorophenyl)-6,7-dihydro-1,2-benzisoxazol-4(5H)-one.

27. The compound as defined in claim 1 which is 5-[2-(4-(4-fluorobenzoyl)-1-piperidinyl)-ethyl]-3-phenyl-6,7-dihydro-1,2-benzisoxazol-4(5H)-one.

28. The compound as defined in claim 1 which is 5-[2-(4-(4-fluorobenzoyl)-1-piperidinyl)-ethyl]-3-(2-fluorophenyl)-6,7-dihydro-1,2-benzisoxazol-4(5H)-one.

29. The compound as defined in claim 1 which is 6,7-dihydro-5-(4-(4-fluorobenzoyl)-1-piperidinyl)methyl-3-(2-fluorophenyl)-1,2-benzisoxazol-4(5H)-one.

30. The compound as defined in claim 1 which is 6,7-dihydro-5-[(4-methyl-1-piperazinyl)methyl]-3-phenyl-1,2-benzisoxazol-4(5H)-one.

31. The compound as defined in claim 1 which is 6,7-dihydro-5-[3-(4-methyl-1-piperazinyl)-propyl]-3-phenyl-1,2-benzisoxazol-4(5H)-one.

32. The compound as defined in claim 1 which is 6,7-dihydro-5-[3-(4-(2-methoxyphenyl)-1-piperazinyl)-propyl]-3-phenyl-1,2-benzisoxazol-4(5H)-one.

33. The compound as defined in claim 1 which is 6,7-dihydro-3-(2-fluorophenyl)-5-[3-(4-(2-methoxyphenyl)-1-piperazinyl)-propyl]-1,2-benzisoxazol-4(5H)-one.

34. The compound as defined in claim 1 which is 3-(4-chlorophenyl)-6,7-dihydro-5-[3-(4-(2-methoxyphenyl)-1-piperazinyl)-propyl]-1,2-benzisoxazol-4(5H)-one.

35. The compound as defined in claim 1 which is 6,7-dihydro-3-(4-fluorophenyl)-5-[3-(4-(2-methoxyphenyl)-1-piperazinyl)-propyl]-1,2-benzisoxazol-4(5H)-one.

36. The compound as defined in claim 1 which is 3-(4-chlorophenyl)-6,7-dihydro-5-[3-(4-(bis-(4-fluorophenyl)methyl)-1-piperazinyl)propyl]-1,2-benzisoxazol-4(5H)-one.

37. The compound as defined in claim 1 which is 6,7-dihydro-5-[3-(4-(bis-(4-fluorophenyl)methyl)-1-piperazinyl)-propyl]-3-(2-fluorophenyl)-1,2-benzisoxazol-4(5H)-one.

38. The compound as defined in claim 1 which is 5-[3-[4-(1,2-benzisothiazol-3-yl)-1-piperazinyl]propyl]-3-(2-fluorophenyl)-6,7-dihydro-1,2-benzisoxazol-4(5H)-one.

39. The compound as defined in claim 1 which is 6,7-dihydro-5-[3-(4-(4-fluorophenyl)-1-piperazinyl)-propyl]-3-(2-fluorophenyl)-1,2-benzisoxazol-4(5H)-one.

40. The compound as defined in claim 1 which is 6,7-dihydro-3-(2-fluorophenyl)-5-[3-(4-(2-pyridyl)-1-piperazinyl)-propyl]-1,2-benzisoxazol-4(5H)-one.

41. The compound as defined in claim 1 which is 5-[3-(4-(3-chlorophenyl)-1-piperazinyl)-propyl]-6,7-dihydro-3-(2-fluorophenyl)-1,2-benzisoxazol-4(5H)-one.

42. The compound as defined in claim 1 which is 6,7-dihydro-3-(2-fluorophenyl)-5-[3-(4-(2-pyrimidyl)-1-piperazinyl)-propyl]-1,2-benzisoxazol-4(5H)-one.

43. The compound as defined in claim 1 which is 6,7-dihydro-3-(2-fluorophenyl)-5-(4-(2-methoxyphenyl)-1-piperazinyl)methyl-1,2-benzisoxazol-4(5H)-one.

44. An antipsychotic composition which comprises a compound as defined in claim 1, present in an amount sufficient to produce an antipsychotic effect, and a pharmaceutically acceptable carrier therefor.

45. A method of treating psychoses which comprises administering to a mammal in need thereof an effective amount of the compound as defined in claim 1.

46. An analgesic composition which comprises a compound as defined in claim 1, present in an analgesically effective amount, and a pharmaceutically acceptable carrier therefor.

47. A method of alleviating pain which comprises administering to a mammal in need thereof an effective amount of the compound as defined in claim 1.

* * * * *

UNITED STATES PATENT AND TRADEMARK OFFICE
CERTIFICATE OF CORRECTION

PATENT NO. : 5,114,936

DATED : May 19, 1992

INVENTOR(S) : David G. Wettlaufer, Gregory M. Shutske and Peter A. Nemoto

It is certified that error appears in the above-identified patent and that said Letters Patent is hereby corrected as shown below:

On the title page, item [57] Abstract, please amend the first formula to appear as follows:

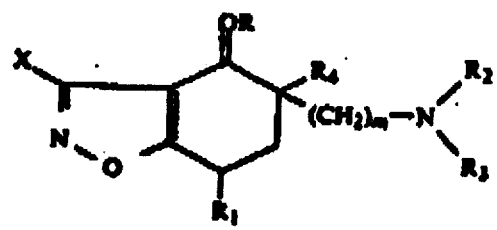

In column 32, lines 60-67, please amend the formula to appear as follows:

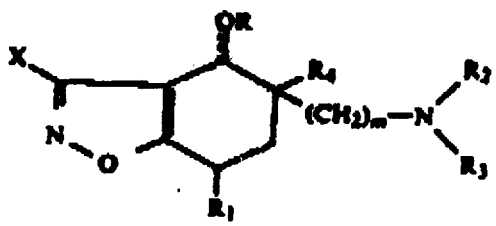

UNITED STATES PATENT AND TRADEMARK OFFICE
CERTIFICATE OF CORRECTION

PATENT NO. : 5,114,936
DATED : May 19, 1992
INVENTOR(S) : David G. Wettlaufer, Gregory M. Shutske and Peter A. Nemoto It is certified that error appears in the above-identified patent and that said Letters Patent is hereby corrected as shown below:

In column 1, lines 12-20, please amend the formula to appear as follows:

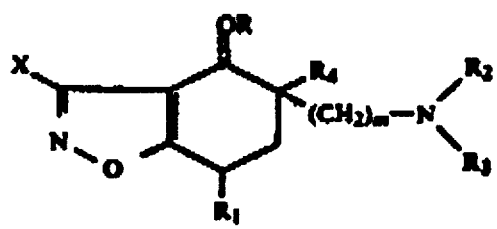

Signed and Sealed this

Eighth Day of December, 1992

Attest:

DOUGLAS B. COMER

Attesting Officer    Acting Commissioner of Patents and Trademarks